US011197787B2

(12) United States Patent
Sheehan

(10) Patent No.: US 11,197,787 B2
(45) Date of Patent: Dec. 14, 2021

(54) ABSORBENT ARTICLE PACKAGE WITH ENHANCED OPENING AND RECLOSEABILITY

(71) Applicant: The Procter & Gamble Company, Cincinnati, OH (US)

(72) Inventor: Astrid Annette Sheehan, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 358 days.

(21) Appl. No.: 16/003,203

(22) Filed: Jun. 8, 2018

(65) Prior Publication Data
US 2018/0289564 A1 Oct. 11, 2018

Related U.S. Application Data

(60) Provisional application No. 61/571,955, filed on Jul. 8, 2011.

(51) Int. Cl.
*B65D 75/06* (2006.01)
*A61F 13/551* (2006.01)
*B65D 75/58* (2006.01)
*B32B 27/08* (2006.01)
*B32B 27/32* (2006.01)
(Continued)

(52) U.S. Cl.
CPC .... *A61F 13/5511* (2013.01); *A61F 13/55115* (2013.01); *B32B 27/08* (2013.01); *B32B 27/32* (2013.01); *B65D 75/06* (2013.01); *B65D 75/52* (2013.01); *B65D 75/5827* (2013.01); *B65D 75/5833* (2013.01); *B65D 85/07* (2018.01);
(Continued)

(58) Field of Classification Search
CPC ............ A61F 13/5511; A61F 13/55105; A61F 13/551; A61F 13/5513; A61F 13/55135; A61F 13/55145; A61F 13/5516; A61F 13/55165; A61F 13/55175; A61F 13/55115; A61F 2013/55195; B65D 85/00; B65D 85/07; B65D 75/00; B65D 75/04; B65D 75/06; B65D 75/5827
See application file for complete search history.

(56) References Cited

U.S. PATENT DOCUMENTS 3,929,678 A 12/1975 Laughlin et al.
4,259,217 A 3/1981 Murphy
(Continued)

FOREIGN PATENT DOCUMENTS

CN 108137207 A 6/2018
EP 0414549 2/1991
(Continued)

OTHER PUBLICATIONS

14850M PCT International Search Report, dated Aug. 17, 2018 (12 pages).

*Primary Examiner* — Steven A. Reynolds
*Assistant Examiner* — Javier A Pagan
(74) *Attorney, Agent, or Firm* — Brian M. Bolam; Christian M. Best

(57) ABSTRACT

A package formed of flexible polymeric film and having a line of weakness to facilitate opening of the package and to demarcate a package base and a package hood is disclosed. The package hood may be configured so as to serve as an effective package reclosure device whereby the package may be used to store the unused supply of articles following opening.

20 Claims, 20 Drawing Sheets

(51) Int. Cl.
*B65D 85/07* (2017.01)
*B65D 75/52* (2006.01)
(52) U.S. Cl.
CPC .... *B32B 2439/40* (2013.01); *B65D 2575/586* (2013.01)

(56) References Cited

U.S. PATENT DOCUMENTS

| | | | |
|---|---|---|---|
| 5,050,742 A * | 9/1991 | Muckenfuhs | B65D 75/5833 |
| | | | 206/494 |
| 5,065,868 A * | 11/1991 | Cornelissen | B65D 33/02 |
| | | | 206/494 |
| 5,179,164 A | 1/1993 | Lausberg et al. | |
| 5,261,899 A | 11/1993 | Visscher et al. | |
| 5,655,843 A * | 8/1997 | Conrad | B65D 33/10 |
| | | | 383/204 |
| 6,258,308 B1 | 7/2001 | Brady et al. | |
| 6,265,512 B1 | 7/2001 | Siedle et al. | |
| 7,910,658 B2 | 3/2011 | Chang et al. | |
| 8,114,522 B2 | 2/2012 | Kitora et al. | |
| 9,169,366 B2 | 10/2015 | Weisman et al. | |
| 2008/0261471 A1 | 10/2008 | Chen et al. | |
| 2009/0255847 A1 | 10/2009 | Motsch et al. | |
| 2010/0062231 A1 | 3/2010 | Abed et al. | |
| 2010/0159167 A1 | 6/2010 | Schumacher | |
| 2012/0237746 A1 | 9/2012 | O'Donnell et al. | |
| 2015/0104627 A1 | 4/2015 | O'Donnell et al. | |
| 2015/0266663 A1 | 9/2015 | Joseph et al. | |
| 2015/0343748 A1 | 12/2015 | Broyles et al. | |
| 2015/0375912 A1 | 12/2015 | Fall | |

FOREIGN PATENT DOCUMENTS

| | | |
|---|---|---|
| EP | 1153848 A1 | 11/2001 |
| JP | H02205546 A | 8/1990 |
| JP | H0699971 A | 4/1994 |
| WO | 9210412 A1 | 6/1992 |
| WO | WO199308874 | 5/1993 |
| WO | WO199308876 | 5/1993 |
| WO | WO2008000411 A1 | 1/2008 |

* cited by examiner

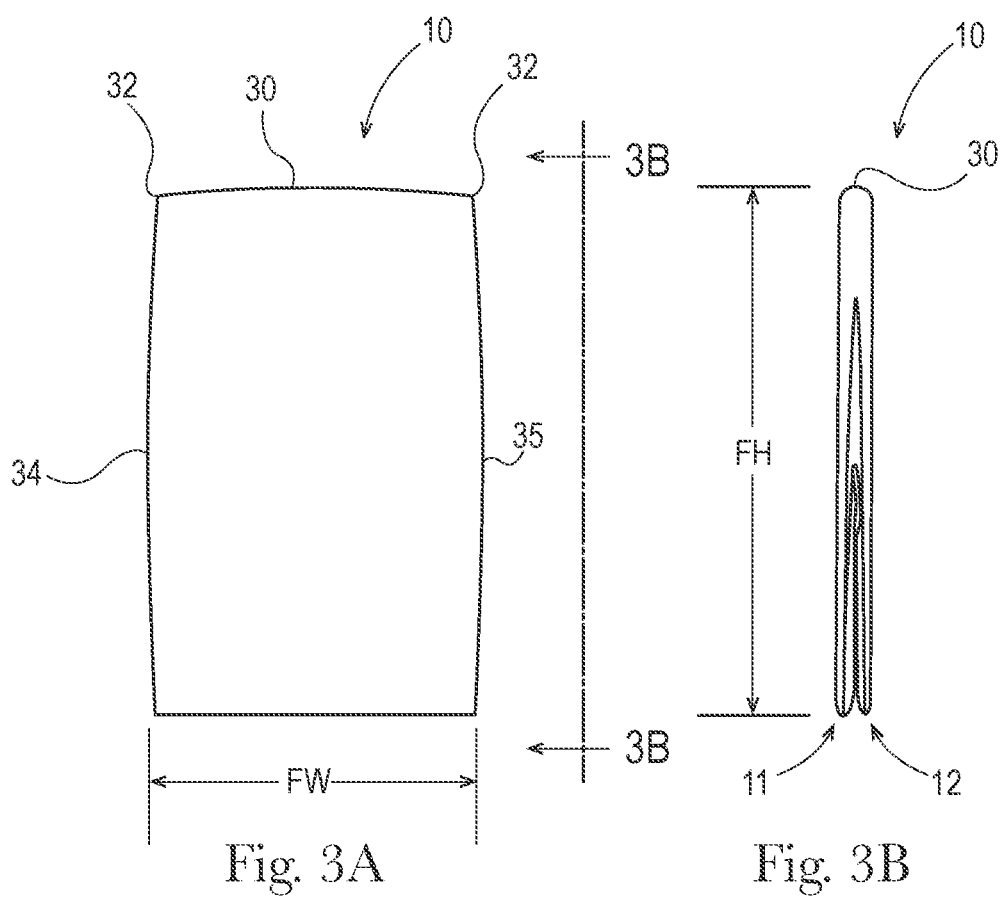

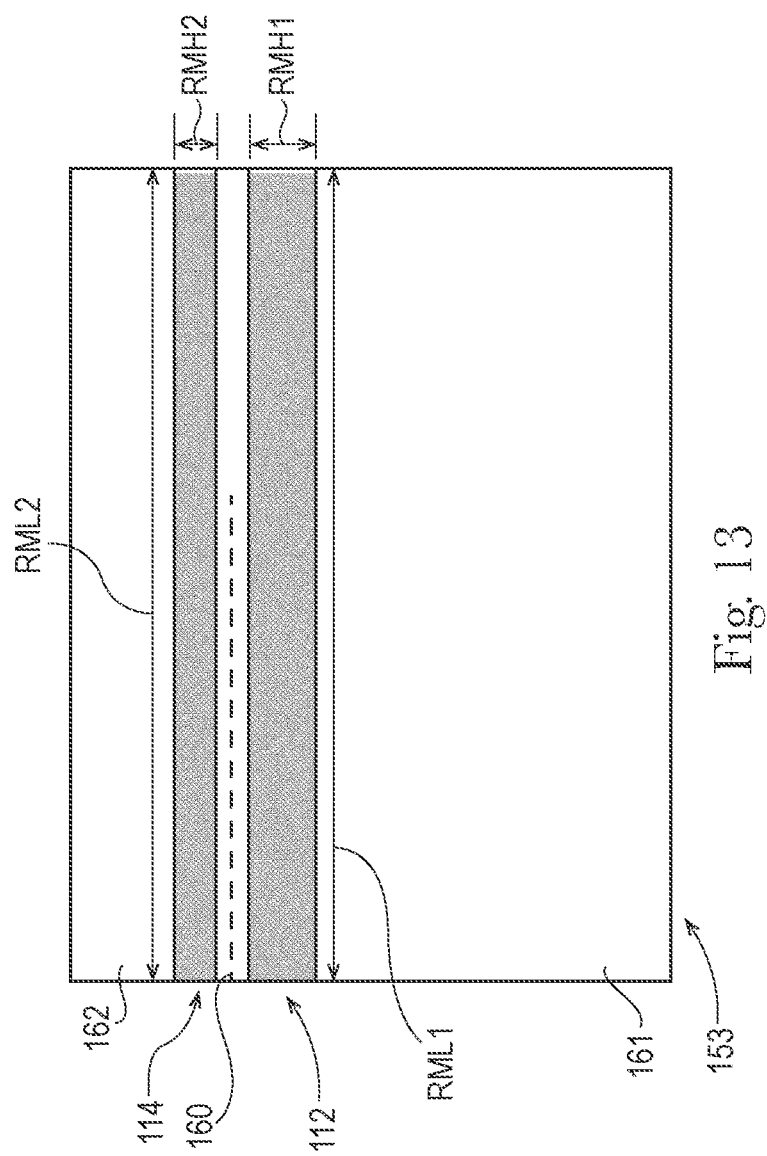

ABSORBENT ARTICLE PACKAGE WITH ENHANCED OPENING AND RECLOSEABILITY

CROSS REFERENCE TO RELATED APPLICATIONS

This application claims the benefit of U.S. Provisional Patent Application No. 62/516,805, filed on Jun. 8, 2017, and of U.S. Provisional Application No. 62/571,955, filed Oct. 13, 2017, which are hereby incorporated by reference.

BACKGROUND OF THE INVENTION

Non-fragile, compressible consumer products such as disposable absorbent articles (e.g., diapers and training pants, disposable adult incontinence pants and feminine hygiene pads) are often packaged and sold at retail (i.e., placed on display and for sale in a retail store) in soft packages formed of polymer film. Such packages may be formed from one or more sheets of polymer film, seamed via application of heating energy, which has caused portions of the film to melt and fuse along the seams.

After opening a package of disposable absorbent articles and removing one or more items needed for immediate use, a consumer may wish to leave the remaining unused supply of product in the package for storage until the next time additional items are needed. Thus, it is often desirable that the package retain, to some extent, its shape and structural integrity to remain useful as a container for storing unused product following opening. Additionally, and particularly in environments where high humidity and substantial quantities of airborne dust and dirt particles may be present, it may be desired that the package not only retain its shape and structural integrity, but have a reclosing capability that allows the package to be reclosed to an extent suitable to help protect the unused product from airborne contaminants.

To date, film package opening features have generally been less than fully satisfactory. Various prior configurations of opening perforations have not provided easy opening features, and in addition or alternatively, tend to promote substantial destruction of the package during opening, rendering it unsatisfactory for use as a storage container. To date, known recloseability features, generally, have not proven to be cost effective for the manufacturer operating in highly competitive markets.

Consequently, there is room for improvement in film package opening features.

BRIEF DESCRIPTION OF THE FIGURES

FIG. 3A is a plan view of the diaper of FIG. 2, shown folded about a lateral fold line, wearer-facing surfaces in and outward-facing surfaces out.

FIG. 3B is an edge side view of the folded diaper shown in FIG. 3A.

FIG. 13 is a side view of a film package surface showing a line of weakness, and a first and second reinforcement member.

FIGS. 14A-14D are schematic plan view depictions of examples of configurations of perforations.

DESCRIPTION OF EXAMPLES

Definitions

Figure 1:
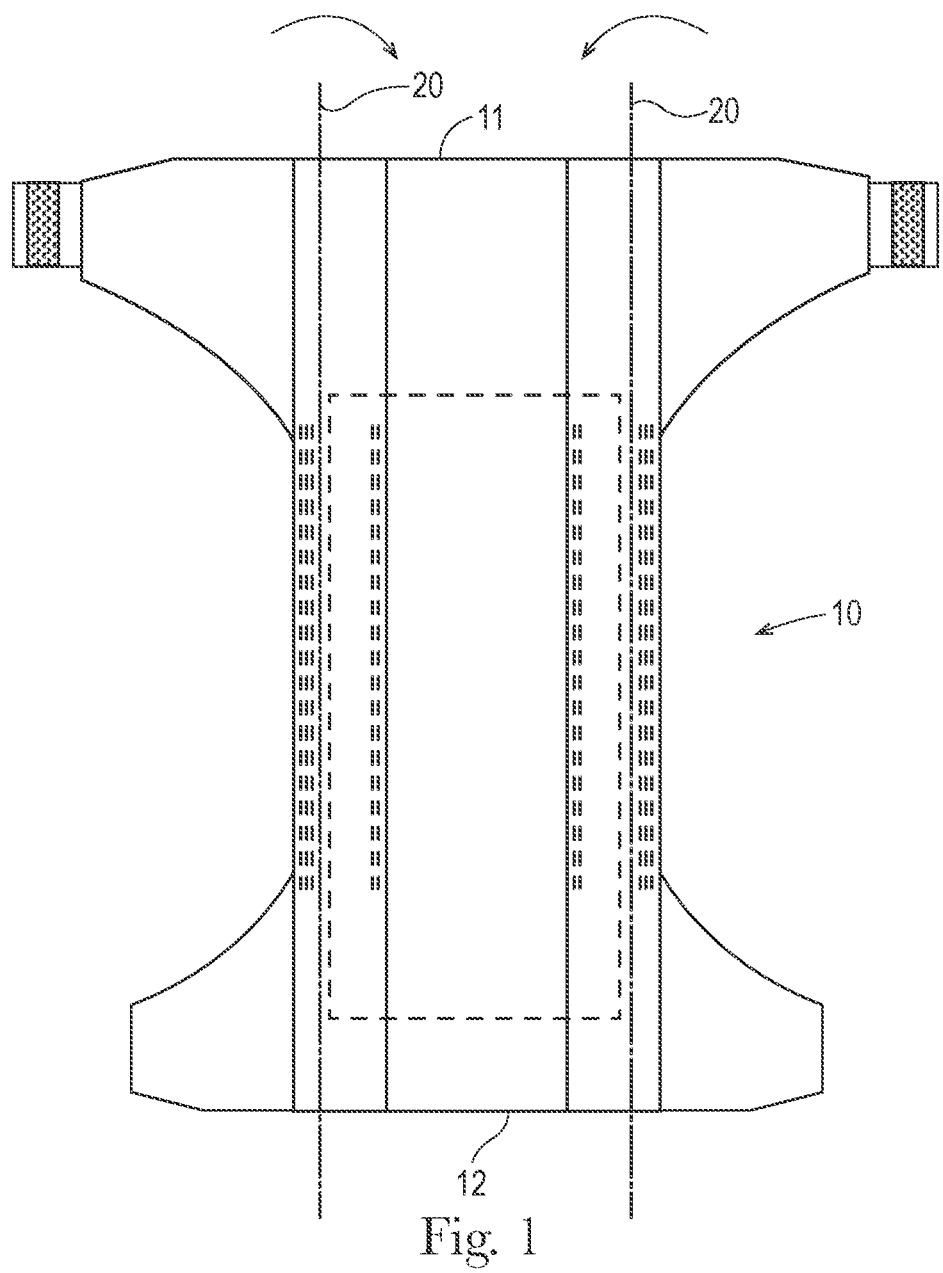
FIG. 1 is a plan view of an example of a disposable absorbent article in the form of a disposable diaper, wearer-facing surfaces facing the viewer.

"Film" means a sheet structure having a length, width and thickness (caliper), wherein each of the length and width greatly exceed the thickness, i.e., by a factor of 1,000 or more, the structure having one layer (monolayer) or more respectively adjacent layers (multilayer), each layer being a substantially continuous structure formed of one or more thermoplastic polymer resins (including blends thereof).

"High Density Polyethylene" (HDPE) means a type of polyethylene defined by a density equal to or greater than 0.941 g/cm$^3$.

"Low Density Polyethylene" (LDPE) means a type of polyethylene defined by a density equal to or less than 0.925 g/cm$^3$.

"Medium Density Polyethylene" (MDPE) means a type of polyethylene defined by a density range of 0.926-0.940 g/cm$^3$.

With respect to a disposable diaper, disposable absorbent pant, or feminine hygiene pad, "lateral" and forms thereof refer to a direction parallel with the waist edges and/or perpendicular to the direction of wearer's standing height when the article is worn.

"Linear Low Density Polyethylene" (LLDPE) means a type of Low Density Polyethylene characterized by substantially linear polyethylene, with significant numbers of short branches, commonly made by copolymerization of ethylene with longer-chain olefins. Linear low-density polyethylene differs structurally from conventional low-density polyethylene (LDPE) because of the absence of long chain branching. The linearity of LLDPE results from the different manufacturing processes of LLDPE and LDPE. In general, LLDPE is produced at lower temperatures and pressures by copolymerization of ethylene and such higher alpha-olefins as butene, hexene, or octene. The copolymerization process produces a LLDPE polymer that has a narrower molecular weight distribution than conventional LDPE and in combination with the linear structure, significantly different rheological properties.

With respect to a disposable diaper, disposable absorbent pant, or feminine hygiene pad, "longitudinal" and forms thereof refer to a direction perpendicular with the waist edges and/or parallel to the direction of the wearer's standing height when the article is worn.

With respect to quantifying the weight fraction or weight percentage of a component of a polymer resin composition forming a film or layer thereof, "predominately" (or a form thereof) means that the component constitutes the largest weight fraction or weight percentage among all components of the composition.

The present invention is directed to packages for containing a plurality of absorbent articles. A non-limiting, representative list of absorbent articles includes diapers, pants, adult incontinence products (liners, pads, pants or underwear), feminine hygiene products (liners and pads), bibs and bed pads. The absorbent articles may be disposable, semi-durable, or durable. The packages are generally formed of a flexible polymer film, which may be a single layer (monolayer) or may have two, three or more layers (multilayer). A multilayer film may have, for example, an outer skin layer formed of a first polymer and an inner skin layer formed of a second polymer. As used herein, the terms "outer" and "inner" refer to the positioning of the layer relative the inside and the outside of the finished package; thus, the "inner layer" faces the contained product, and the "outer layer" faces outward and has an outer surface that is exposed to view and touch by, e.g., shoppers in a retail store.

Exemplary Absorbent Articles

Figure 2:
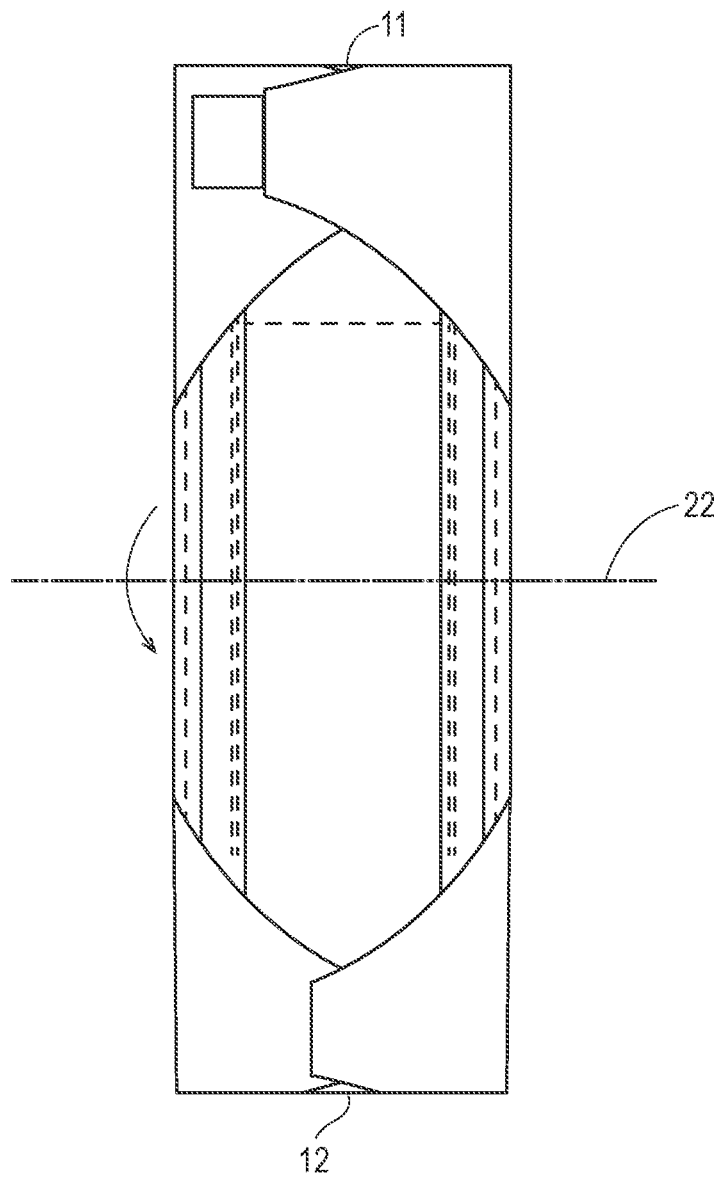
FIG. 2 is a plan view of the diaper of FIG. 1, shown with side portions folded over and laterally inward about longitudinal side edge fold lines.
Figure 4A:
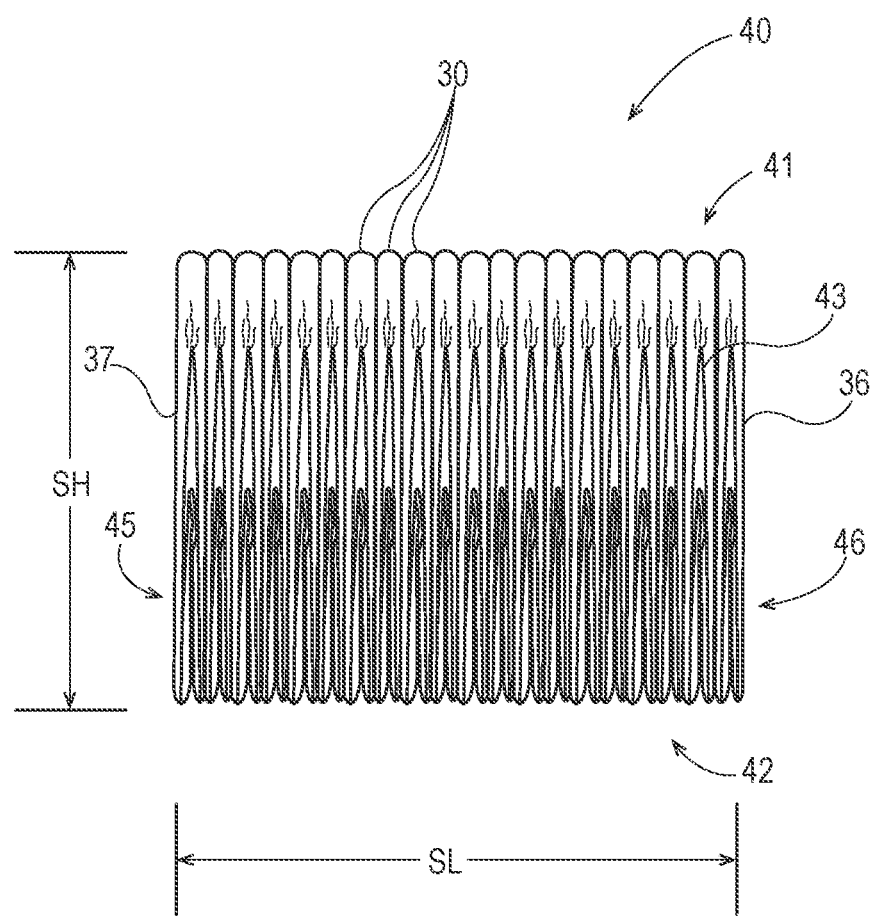
FIG. 4A is an edge side view of a stack of a plurality of folded diapers such as the folded diaper shown in FIGS. 3A and 3B.
Figure 4B:
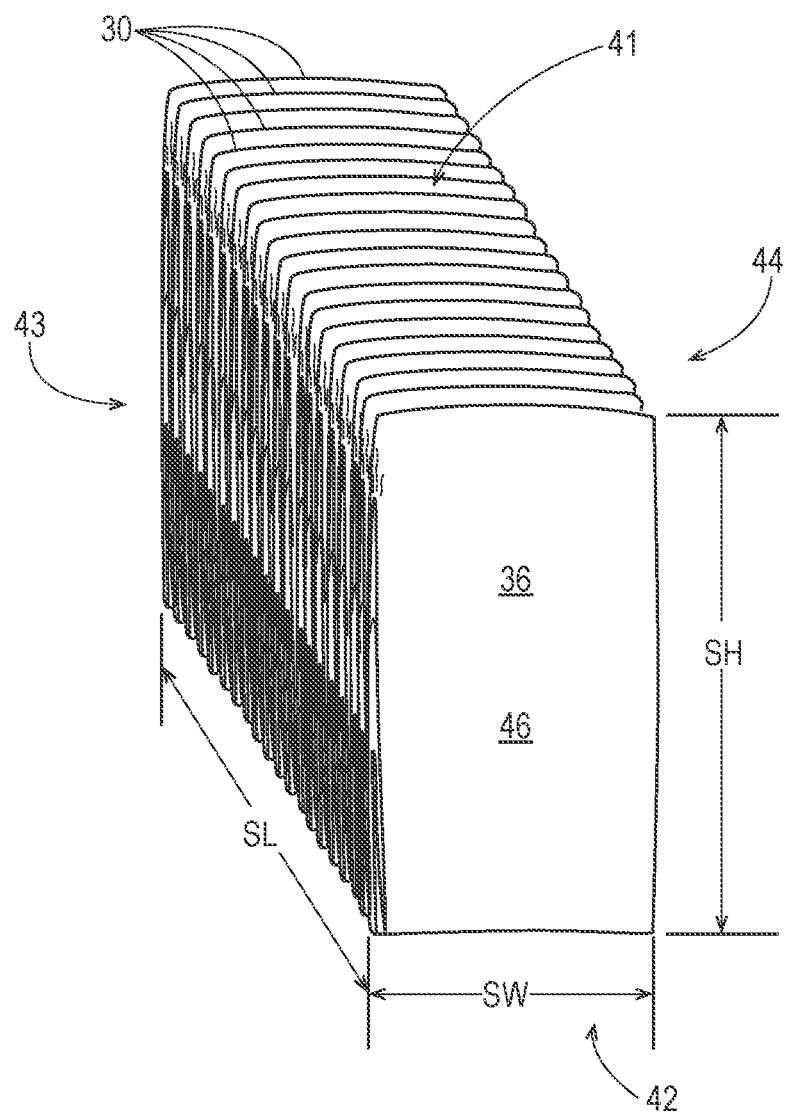
FIG. 4B is a perspective view of the stack of FIG. 4A.

FIGS. 1-3 depict an example of a disposable diaper with front and rear waist edges 11, 12, in successively open/unfolded and folded. FIGS. 4A and 4B depict a stack of a plurality of disposable diapers such that depicted in FIGS. 1-3. For packaging in bulk, each of a plurality of disposable diapers such as that shown in FIG. 1 may, in a possible first step, have its longitudinal side portions be folded over and laterally inward about longitudinal side edge fold lines 20, as may be appreciated from a comparison of FIGS. 1 and 2. Next, the diaper may, in a second step, be folded longitudinally, about lateral fold line 22 that passes through the crotch region of the diaper, as may be appreciated from a comparison of FIGS. 2 and 3. For a bi-fold configuration such as depicted in FIGS. 3A, 3B and 4, the article may be folded longitudinally once, and may in some examples be folded approximately in half about the lateral fold line. For a tri-fold configuration (not shown), the article may be folded longitudinally twice, about two longitudinally-spaced lateral fold lines. In some examples a tri-fold configuration may have the article folded approximately in thirds, about the two longitudinally-spaced lateral fold lines.

Regardless of whether the article is in a bi-fold or tri-fold configuration, the folded article such as folded diaper 10 will have a single fold nose 30 defining at least one end edge of the folded article, fold nose corners 32, and left and right side edges 34, 35. (It will be appreciated that in a tri-fold example, a single fold nose may define each of both end edges of the folded article.) In some examples such as depicted in FIGS. 3A and 3B, fold nose 30 may be proximate the crotch region of the article (the middle region of the article adapted to be located between the wearer's legs during wear). The folded article will have a folded width FW measured as the distance between side edges, and a folded height FH measured as the distance between end edges. A plurality of folded articles such as depicted in FIGS. 3A and 3B may then be placed in similar orientation and neatly stacked together face-to-face to form a stack 40 such as depicted in FIGS. 4A and 4B. In another example (not shown), a first set of the plurality of folded articles may have their fold noses oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack. For purposes of economy of space in packaging, packing, shipping and shelving, stack 40 may be compressed to a desired degree of compression, along the stack direction SD.

Referring to FIGS. 4A and 4B, stack 40 will have an approximate rectangular cuboid form with a stack height SH approximately corresponding to the folded height FH of the individual folded articles, a stack width SW approximately corresponding to the folded width FW of the individual folded articles, and a stack length SL measured from a first outward-facing side 36 of a first article in the stack to an opposing second outward-facing side 37 of a last article in the stack, along stacking direction SD. Stack 40 may have a first side 41 and an opposing second side 42, one or both of which are defined by approximately aligned fold noses of folded articles in the stack. Stack 40 may have opposing third and fourth sides 43, 44, both of which are defined by approximately aligned side edges 34, 35 of folded articles in the stack. Stack 40 may have opposing fifth and sixth sides 45, 46, each of which is defined by one of first and second outward facing sides 36, 37 of first and last articles at each end of the stack.

Exemplary Package Structures

Figure 5A:
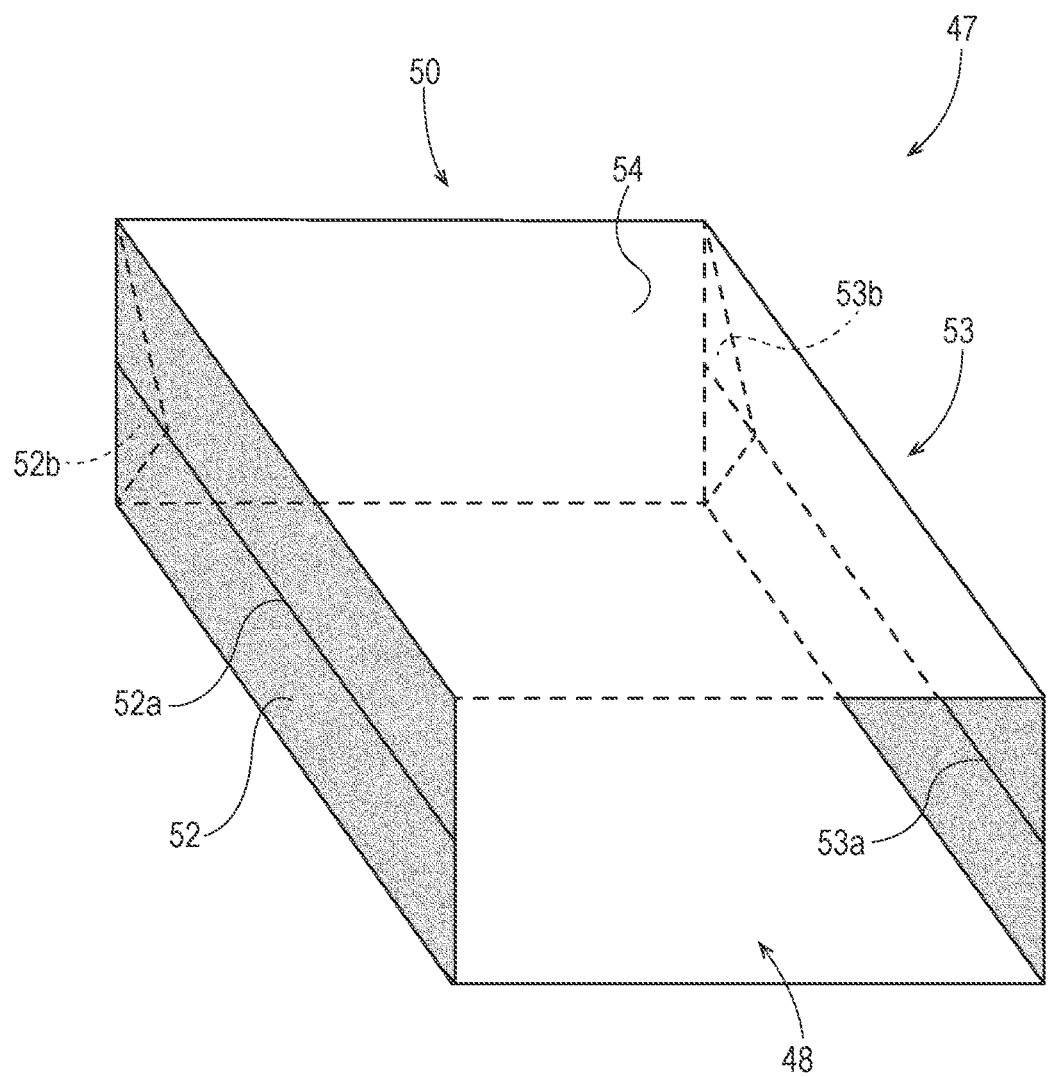
FIG. 5A is a perspective view of a film bag structure from which a film package may be formed.
Figure 5B:
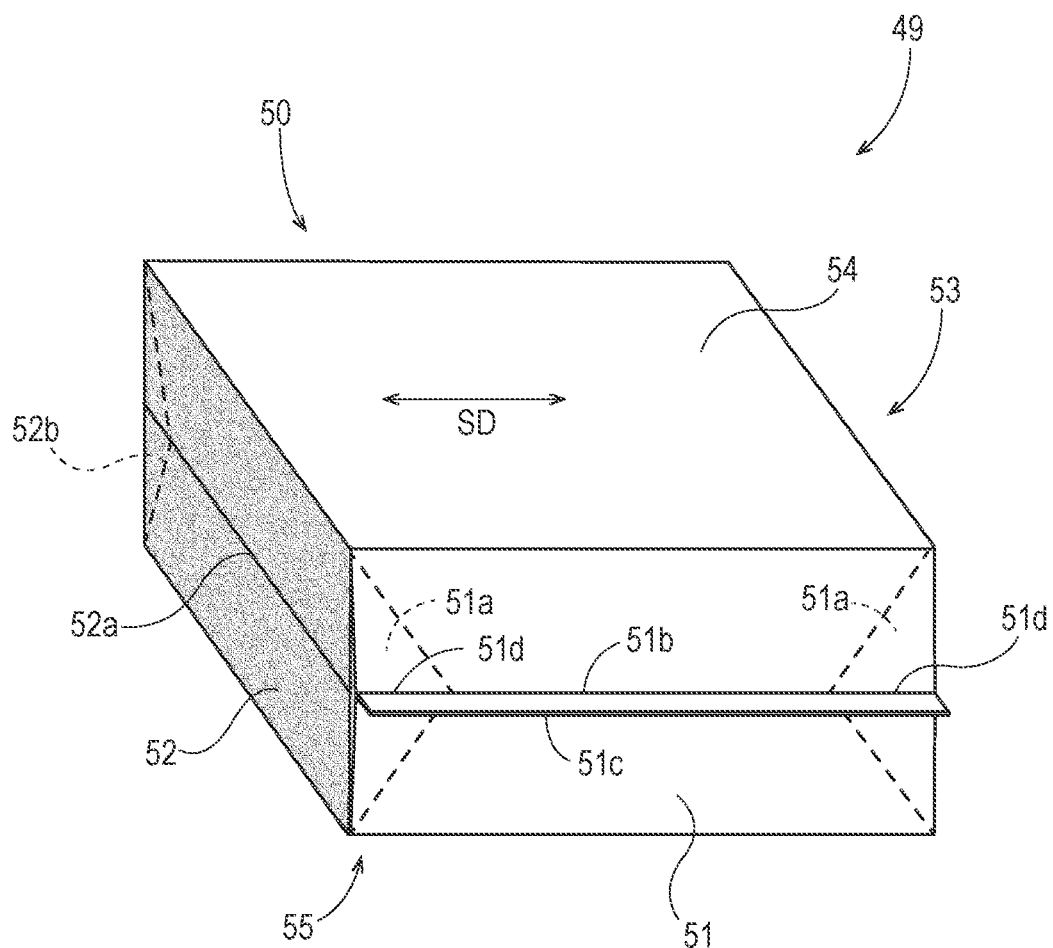
FIG. 5B is a perspective view of a film package that may be used to contain a stack of disposable absorbent articles such as the stack shown in FIG. 4.
Figure 5C:
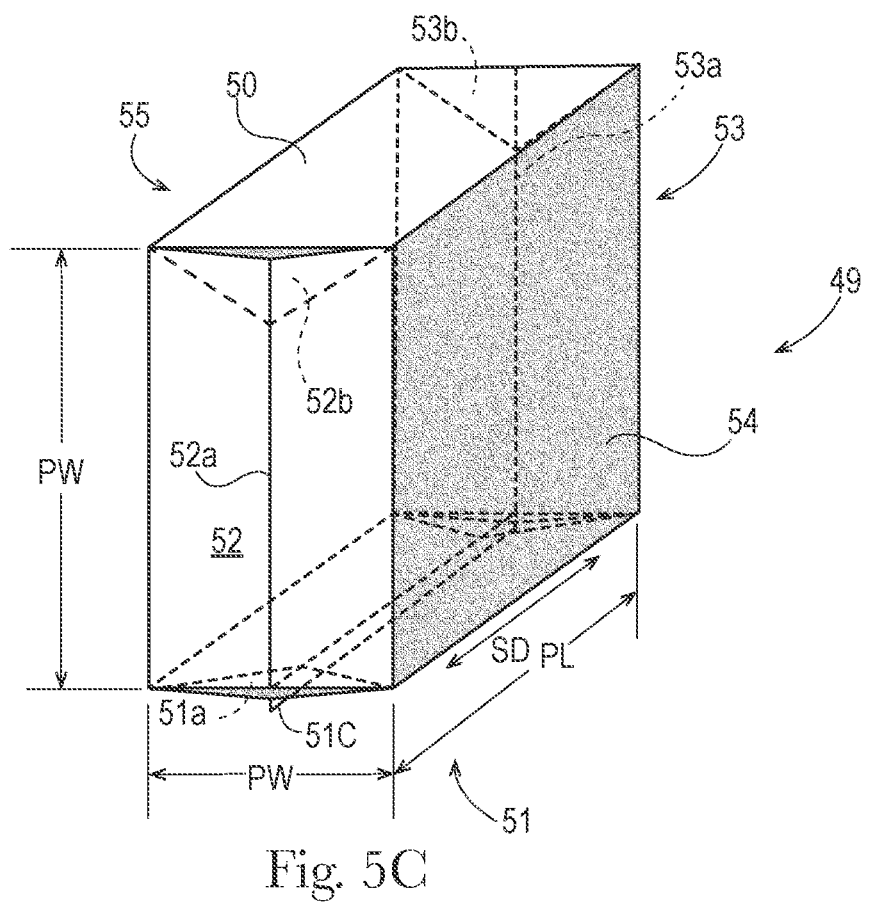
FIG. 5C is an alternative perspective view of the film package shown in FIG. 5B.

Referring to FIG. 5A, an exemplary bag structure 47 may be formed from a single sheet of film stock that is suitably folded to form bag gussets 52b, 53b and then joined along portions by bonding to form two side seams 52a, 53a on opposite sides, to form bag structure 47 with no seam on a first package surface 50, and open at the other end 48 (e.g., a gusseted bag structure). Thereafter, the bag structure may be filled by inserting product such as stack 40 of diapers through the open end 48. In a first example, stack 40 of diapers may be inserted first side 41 first, such that after insertion the fold noses inside the package are adjacent first package surface 50. In another example, stack 40 of diapers may be inserted first side 41 last (i.e., second side 42 first), such that after insertion the fold noses inside the package are adjacent second package surface 51. As may be appreciated from FIGS. 5B and 5C, the open end 48 opposite first package surface 50 may then be closed by suitably folding to form closing gussets 51a, bringing the film edges together, and bonding them together to form end seam 51b and second package surface 51. The bag structure 47 and stack 40 dimensions may be suitably selected and effected through design, folding, stacking, compression and packaging processes such the film of the package is taut about the stack at least along the stacking direction SD, to retain the individual diapers 10 in place within the stack 40, maintain stack compression, and maintain a neat, stable, approximate rectangular cuboid shape for the stack 40, and as a result, the package 49. Because the package 49 is formed of flexible polymer film, when suitably sized relative to the stack 40 dimensions, package 49 will approximately assume the approximate rectangular cuboid shape and dimensions of the stack 40, when the package film is taut, or otherwise when any loose film is pressed against the stack. When the package film is taut about the stack along directions generally parallel with the stacking direction, in a manner that helps maintain stack compression along the stacking direction, the package will have a package length PL approximately corresponding to the stack length SL, and a package width approximately corresponding to the stack width SW. If the package structure is sized to provide no head space adjacent one or both of first and second sides 41, 42 of packaged stack 40 (i.e., no slack is present in the package film adjacent first and second sides 41, 42 of the stack after the package 49 is formed), the package will have a package height PH approximately corresponding to the stack height SH. In some examples, however, the film package structure may be sized to provide head space, and correspondingly, slack film, adjacent one or both of the first 41 and second 42 sides of stack 40, such as may be desired to provide a hood structure (described below) with extra height and overlapping capability.

To which reference is made above, the left and right side edges 34, 35 of the folded diapers in the stack 40, and corresponding third and fourth sides 43, 44 of stack 40 will be adjacent fifth and/or sixth package surfaces 54 and 55. It may be desired that the stack size and bag configuration and dimensions be selected such that fifth and sixth package surfaces 54 and 55 are the largest surfaces, or front and rear "faces," of the package. In this arrangement, when the film of the package is taut about the stack, the film of the third, fourth, fifth and sixth package surfaces 52, 53, 54 and 55 is in tension along directions approximately parallel to the approximate plane of the first surface 50, serving to at least partially maintain any compression of the stack 40 along the stacking direction SD.

In some examples, the film stock may be supplied preprinted with desired commercial artwork, graphics, trademark(s) and/or verbal or graphic product information, prior to formation of the bag structure.

The bonds forming any or all of the seams such as seams 52a, 53a and 51b may be created by welding. (Herein, "weld" refers to a union between separate portions of film stock, effected by application of direct or indirect (e.g., ultrasonic) heating energy and pressure that causes separate portions of the film to at least partially melt and fuse together to some extent, forming a bonded area, joint or seam which cannot be separated without substantial destruction to the remainder of one or both joined portions.) If bag-forming and/or packaging machinery forms welds in the film that join the film stock to itself by applying heating energy that causes the film to fuse to itself, it may be desirable that the film stock be multilayer film, and that the layer(s) to be brought into contact and fused be formed of polymer(s) that have lower melting temperature(s) than those of the polymer(s) used to form the other layer(s). This enables heating energy to be applied to a degree sufficient to heat the layer(s) in contact and cause them to fuse, but not sufficient to cause undesired melting and deformation of the other layer(s), which could cause the package to be misshapen and/or displace and/or distort printing on the film stock.

A multilayer film may be co-formed (such as by coextrusion), or in another example, individual layers may be separately formed and then laminated together following their formation, by use of a suitable laminating adhesive. In this latter example, an advantage provided is that one of the layers may be printed on one side before lamination. Following that, the printed side may be faced inward (facing the other layer(s)) during lamination, such that it is protected by the other layer(s) from abrasion and wear in the finished film product, thereby preserving the integrity of the printed images, graphics, verbal content, etc. A suitable multilayer film may be formed of one or more polyolefins, such as polypropylene and polyethylene. In one example, the stock film may have at least two layers, including a first layer of predominately polyethylene and second layer of predominately polypropylene. In one example, a layer formed of predominately polypropylene having a first relatively higher melting temperature, and a layer of predominately polyethylene having a second relatively lower melting temperature, may be used to form the outer and inner layers, respectively. In another example, an inner layer may be formed predominately of a first type of polyethylene having a relatively lower melting temperature, and an outer layer may be formed predominately of a second type of polyethylene having a relatively higher melting temperature.

In an application such as described herein, a multilayer film may be preferred. A multilayer film may have layers of polymer compositions particularly chosen for the characteristics they impart to the film. For example, one or two outer skin layers may be formed of compositions chosen for, e.g., surface gloss; printability; smooth feel; pliability; low noise generation (upon being handled and manipulated, as by a consumer); relatively lower melt temperature and fusibility/weldability; or any combination of these characteristics. One or more intermediate layers may be formed of compositions chosen for, e.g., tensile strength; stiffness; toughness; suitability for inclusion of blended-in recycled material; environmentally-friendly and/or sustainable material sourceability; relatively higher melt temperature; co-extrusion compatibility with adjacent layers (such that strong bonding between layers occurs upon co-extrusion); or any combination of these characteristics. For film stock in which only one side of the film will be placed in contact with itself and welded, a two-layer film may suffice. For film stock in which both sides of the film will be placed in contact with itself and welded, a film having at least three layers, with two outside skin layers that are weldable, may desired. It will be appreciated that a package having the configuration depicted in FIGS. 5B and 5C requires the film to be welded to itself on both sides—on the generally outer film surface at the gussets 51a, 52b and 53b, and on the generally inner film surface along all other portions of the seams 51b, 52a and 53a.

Film Composition

A multilayer film may include first outside skin layer, second outside skin layer, and intermediate layer disposed between the skin layers.

Each of the layers may include a base polymer. Base polymers may include polyolefins, particularly polyethylenes, polypropylenes, polybutadienes, polypropylene-ethylene interpolymer and copolymers having at least one olefinic constituent, and any mixtures thereof. Certain polyolefins can include linear low density polyethylene (LLDPE), low density polyethylene (LDPE), medium density polyethylene (MDPE), high density polyethylene (HDPE), isotactic polypropylene, random polypropylene copolymers, impact modified polypropylene copolymer, and other polyolefins which are described in PCT Application Nos. WO 99/20664, WO 2006/047374, and WO 2008/086539.Other base polymers such as polyesters, nylons, polyhydroxyalkanoates (or PHAs), copolymers thereof, and combinations of any of the foregoing may also be suitable. In addition, polyolefin plastomers and elastomers could be used to form the multilayer polymeric films. Examples of such suitable polyolefin plastomers and elastomers are described in U.S. Pat. No. 6,258,308; U.S. Publication No. 2010/0159167 A1; and PCT Application Nos. WO 2006/047374 and WO 2006/017518. In one embodiment, such polyolefin plastomers and/or elastomers may comprise up to 25% by volume of the multilayer polymeric film. Other useful polymers include poly-α-olefins such as those described in PCT Application No. WO 99/20664 and the references described therein.

In some examples, one or both of the skin layers may be formed of predominately MDPE, LDPE or LLDPE, more preferably LLDPE. A skin layer formed of predominately LLDPE may be particularly preferred because it imparts the skin layer with a good combination of weldability, relatively low melt temperature, printability (compatibility with currently commercially available printing inks), smooth surface finish, low noise, and a soft and pliable feel. In some examples, an intermediate layer may be formed of predominately HPDE, MDPE or LDPE, more preferably MDPE.

An intermediate layer formed of predominately MDPE may be particularly preferred with one or more skin layers formed predominately of LLDPE because it imparts the intermediate layer with a good combination of relatively higher melt temperature, co-extrusion compatibility with the skin layer(s), pliability, toughness and tensile strength.

In alternative examples, an intermediate layer may be formed partially or predominately of a thermoplastic polymer other than polyethylene, such as any of the polymers identified above, or any polymers identified as suitable for intermediate layers in, for example, U.S. Pats. Nos. 9,169,366 and 5,261,899; and U.S. Pat. Apps. Pub. Nos. 2015/03433748; 2015/0104627; and 2012/0237746, including bio-polymers or polymers having bio-based content as described in the latter three publications, such as, but not limited to, polylactic acid and thermoplastic starch. Additionally, an intermediate layer may include recycled thermoplastic polymer of any of the above-described types.

For purposes of balancing economy of polymer usage and maximization of tensile strength of the film, it may be desired that the total caliper of the film fall within a range of from 40 μm to 100 μm, more preferably from 50 μm to 90 μm, and even more preferably from 60 μm to 80 μm. For purposes of balancing economy of polymer usage, tensile strength and weldability, it may be desired that a three-layer film as described herein have a first and second skin layers each constituting from 15 percent to 35 percent of the weight of the film, and an intermediate layer constituting from 30 percent to 70 percent of the weight of the film.

A multi-layer film as contemplated herein may comprise one or more tie layers disposed between other layers. A tie layer may be necessary when the polymers of adjoining layers would not otherwise be miscible or compatible so as to bond to each other during extrusion. For example, a tie layer between a polyethylene skin layer and an intermediate layer having a large polylactic acid content may be deemed desirable. Thus, for example, in a multilayer film having three main layers—two skin layers and an intermediate layer disposed between them, tie layers may be disposed between the intermediate layer and each of the skin layers. A tie layer may include one or more functionalized polyolefins. In some example, a tie layer may include from 5%, 10%, 20%, 30%, 40% or 45% to 55%, 60%, 70%, 80%, 90%, or 100%, by weight of the tie layer, of the one or more functionalized polyolefins. A tie layer may consist essentially of the one or more functionalized polyolefins.

For example, because of the significant difference in polarity between polylactic acid (PLA) and polyolefins, blends of these components typically result in incompatible systems with poor physical properties. A multilayer film having predominately polyethylene skin layers sandwiching an intermediate layer including PLA may also include one or more tie layers between the skin layers and the intermediate layer. This particular multi-layer structure may provide the MD and/or CD tensile properties useful for products currently made from polyethylene while incorporating a renewable feedstock (PLA). This arrangement may also enable downgauging (i.e., caliper reduction or basis weight reduction) of the film resulting from improvements in stiffness that can be used to drive sustainability and/or used as a cost savings.

The tie layer may comprise a functionalized polyolefin that possesses a polar component provided by one or more functional groups that is compatible with the PLA of the intermediate layer(s) and a non-polar component provided by an olefin that is compatible with one or more polyolefins of the adjacent skin layer. The polar component may, for example, be provided by one or more functional groups and the non-polar component may be provided by an olefin. The olefin component may generally be formed from any linear or branched α-olefin monomer, oligomer, or polymer (including copolymers) derived from an olefin monomer. The α-olefin monomer typically has from 2 to 14 carbon atoms and preferably from 2 to 6 carbon atoms. Examples of suitable monomers include, but not limited to, ethylene, propylene, butene, pentene, hexene, 2-methyl-1-propene, 3-methyl-1-pentene, 4-methyl-1-pentene, and 5-methyl-1-hexene. Examples of polyolefins include both homopolymers and copolymers, i.e., polyethylene, ethylene copolymers such as EPDM, polypropylene, propylene copolymers, and polymethylpentene polymers.

An olefin copolymer can include a minor amount of non-olefinic monomers, such as styrene, vinyl acetate, diene, or acrylic and non-acrylic monomer. Functional groups may be incorporated into the polymer backbone using a variety of known techniques. For example, a monomer containing the functional group may be grafted onto a polyolefin backbone to form a graft copolymer. Such grafting techniques are well known in the art and described, for instance, in U.S. Pat. No. 5,179,164. In other embodiments, the monomer containing the functional groups may be copolymerized with an olefin monomer to form a block or random copolymer. Regardless of the manner in which it is incorporated, the functional group of the compatibilizer may be any group that provides a polar segment to the molecule, such as a carboxyl group, acid anhydride group, acid amide group, imide group, carboxylate group, epoxy group, amino group, isocyanate group, group having oxazoline ring, hydroxyl group, and so forth. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation POLYBOND and Eastman Chemical Company under the designation Eastman G SERIES, and AMPLIFY™ GR Functional Polymers (maleic anhydride grafted polyolefins). Other examples include LOTADER AX8900 (polyethylene-methyl acrylate-glycidyl methacrylate terpolymer) and LOTADER TX 8030 (polyethylene-acrylic ester- maleic anhydride terpolymer) available from Arkema, Columbes, France.

In some aspects, the tie layer can be a resin composition as disclosed in U.S. Pat. No. 8,114,522. This resin composition includes a modified PO resin and a terpene resin. Alternatively, it includes a polylactic acid resin, a modified polyolefin resin, and a hydrogenated petroleum resin. These compositions are suitable for use as a tie layer between the outer layer and the core layer.

In some examples, an outer layer and tie layer may be essentially combined as an outer layer by incorporating a functionalized polyolefin into one or both of the outer layers. In these instances, the multi-layer film may comprise 3 or 4 layers. In the case of a 3 layer film, the film may comprise a first outer layer comprising a polyolefin and/or a functionalized polyolefin, one or more core layers, and a second outer layer comprising a polyolefin and/or a functionalized polyolefin). In the case of a 4 layer film, the film may comprise a first outer layer comprising a polyolefin and/or a functionalized polyolefin, one or more core layers, a tie layer, and a second outer layer comprising a polyolefin.

Any of the layers of the multi-layer film may comprise small amounts of one or more additives. Typically, the additives may comprise less than about 10%, 5%, 4%, 3%, 2%, 1%, 0.5%, 0.1% or 0.01% by weight of the layer of the additive. Some non-limiting examples of classes of additives contemplated include perfumes, dyes, pigments, nanoparticles, antistatic agents, fillers, and combinations thereof. The layers disclosed herein can contain a single additive or a mixture of additives. For example, both a perfume and a colorant (e.g., pigment and/or dye) can be present.

A pigment or dye can be inorganic, organic, or a combination thereof. Specific examples of pigments and dyes contemplated include pigment Yellow (C.I. 14), pigment Red (C.I. 48:3), pigment Blue (C.I. 15:4), pigment Black (C.I. 7), and combinations thereof. Specific contemplated dyes include water soluble ink colorants like direct dyes, acid dyes, base dyes, and various solvent soluble dyes. Examples include, but are not limited to, FD&C Blue 1 (C.I. 42090:2), D&C Red 6(C.I. 15850), D&C Red 7(C.I. 15850: 1), D&C Red 9(C.I. 15585: 1), D&C Red 21(C.I. 45380:2), D&C Red 22(C.I. 45380:3), D&C Red 27 (C.I. 45410: 1), D&C Red 28(C.I. 45410:2), D&C Red 30(C.I. 73360), D&C Red 33(C.I. 17200), D&C Red 34(C.I. 15880: 1), and FD&C Yellow 5(C.I. 19140: 1), FD&C Yellow 6(C.I. 15985: 1), FD&C Yellow 10(C.I. 47005: 1), D&C Orange 5(C.I. 45370:2), and combinations thereof.

Contemplated fillers include, but are not limited to, inorganic fillers such as, for example, the oxides of magnesium, aluminum, silicon, and titanium. These materials can be added as inexpensive fillers or processing aides. Other inorganic materials that can function as fillers include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, can be used. Additionally, alkyd resins can also be added to the composition. Alkyd resins can comprise a polyol, a polyacid or anhydride, and/or a fatty acid.

Additional contemplated additives include nucleating and clarifying agents for the thermoplastic polymer. Specific examples, suitable for polypropylene, for example, are benzoic acid and derivatives (e.g., sodium benzoate and lithium benzoate), as well as kaolin, talc and zinc glycerolate. Dibenzlidene sorbitol (DBS) is an example of a clarifying agent that can be used. Other nucleating agents that can be used are organocarboxylic acid salts, sodium phosphate and metal salts (e.g., aluminum dibenzoate). In one aspect, the nucleating or clarifying agents can be added in the range from 20 parts per million (20 ppm) to 20,000 ppm, or from 200 ppm to 2000 ppm, or from 1000 ppm to 1500 ppm. The addition of the nucleating agent can be used to improve the tensile and impact properties of the finished composition.

Additional contemplated additives include slip agents for purposes of reducing the coefficient of friction on one or both of the two outside surfaces of the film, or as antiblocking agents. Suitable additives for this purpose may include but are not limited to fatty amides, for example, erucamide.

Additives may also include antioxidants such as BHT, and IRGANOX products, for example, IRGANOX 1076 and IRGANOX 1010. IRGANOX products are available from BASF Corporation, Florham Park, N.J., USA. Antioxidants may help reduce degradation of the film through oxidation, particularly during processing.

Contemplated surfactants include anionic surfactants, amphoteric surfactants, or a combination of anionic and amphoteric surfactants, and combinations thereof, such as surfactants disclosed, for example, in U.S. Pat. Nos. 3,929, 678 and 4,259,217, and in EP 414 549,WO93/08876, and WO93/08874.

Contemplated nanoparticles include metals, metal oxides, allotropes of carbon, clays, organically modified clays, sulfates, nitrides, hydroxides, oxy/hydroxides, particulate water-insoluble polymers, silicates, phosphates and carbonates. Examples include silicon dioxide, carbon black, graphite, grapheme, fullerenes, expanded graphite, carbon nanotubes, talc, calcium carbonate, bentonite, montmorillonite, kaolin, zinc glycerolate, silica, aluminosilicates, boron nitride, aluminum nitride, barium sulfate, calcium sulfate, antimony oxide, feldspar, mica, nickel, copper, iron, cobalt, steel, gold, silver, platinum, aluminum, wollastonite, aluminum oxide, zirconium oxide, titanium dioxide, cerium oxide, zinc oxide, magnesium oxide, tin oxide, iron oxides (Fe203, Fe304) and mixtures thereof. Nanoparticles can increase strength, thermal stability, and/or abrasion resistance of the compositions disclosed herein, and can give the compositions electric properties.

Contemplated anti-static agents include fabric softeners that are known to provide antistatic benefits. These can include those fabric softeners having a fatty acyl group that has an iodine value of greater than 20, such as N,N-di(tallowoyl-oxy-ethyl)-N,N-dimethyl ammonium methylsulfate.

In particular aspects, the filler can comprise renewable fillers. These can include, but are not limited to, lipids (e.g., hydrogenated soybean oil, hydrogenated castor oil), cellulosics (e.g., cotton, wood, hemp, paperboard), lignin, bamboo, straw, grass, kenaf, cellulosic fiber, chitin, chitosan, flax, keratin, algae fillers, natural rubber, nanocrystalline starch, nanocrystalline cellulose, collagen, whey, gluten, and combinations thereof.

Particular combinations of film layers, film layer compositions and pigment additives for maximizing package film opacity while providing a film that effectively balances weldability, tensile strength and cost effectiveness are described in PCT Application No. CN2016/088098, the disclosure of which is incorporated herein by reference.

Opening Features

Figure 6A:
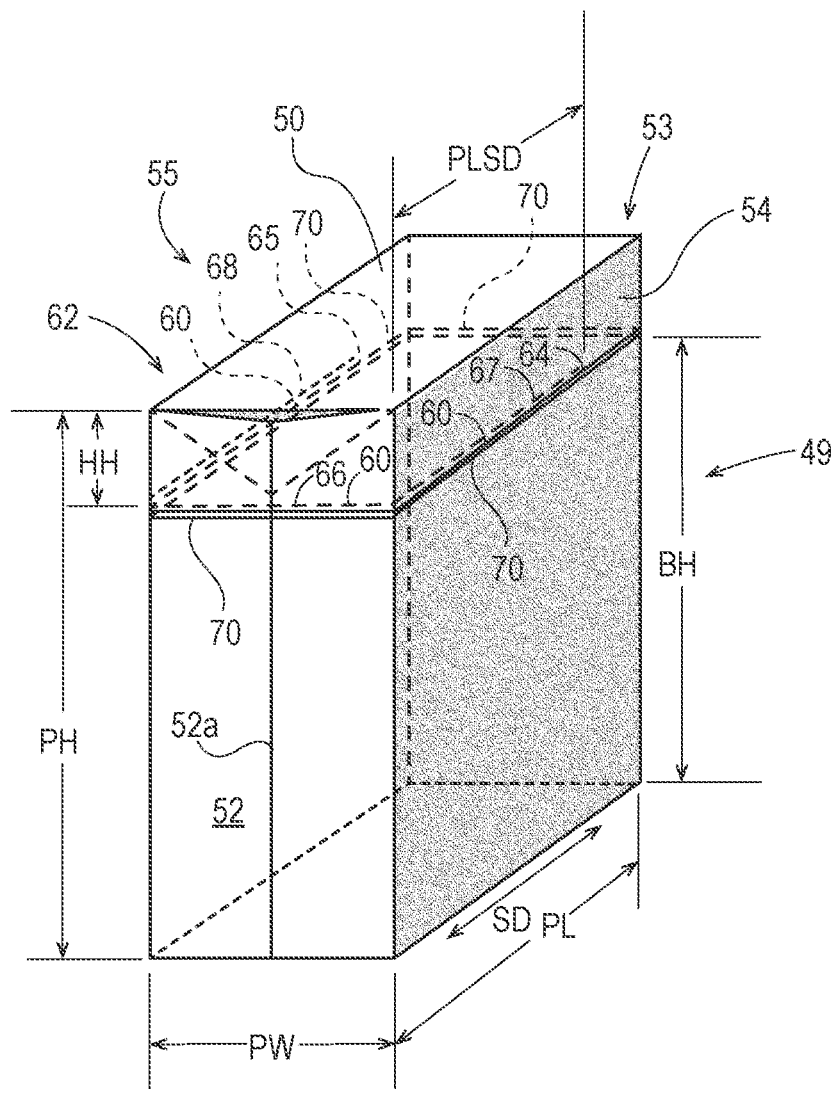
FIG. 6A is a perspective view of a film package that may be used to contain a stack of diapers such as the stack shown in FIG. 4, depicting a configuration of a line of weakness of perforations or scoring, in one example.
Figure 7A:
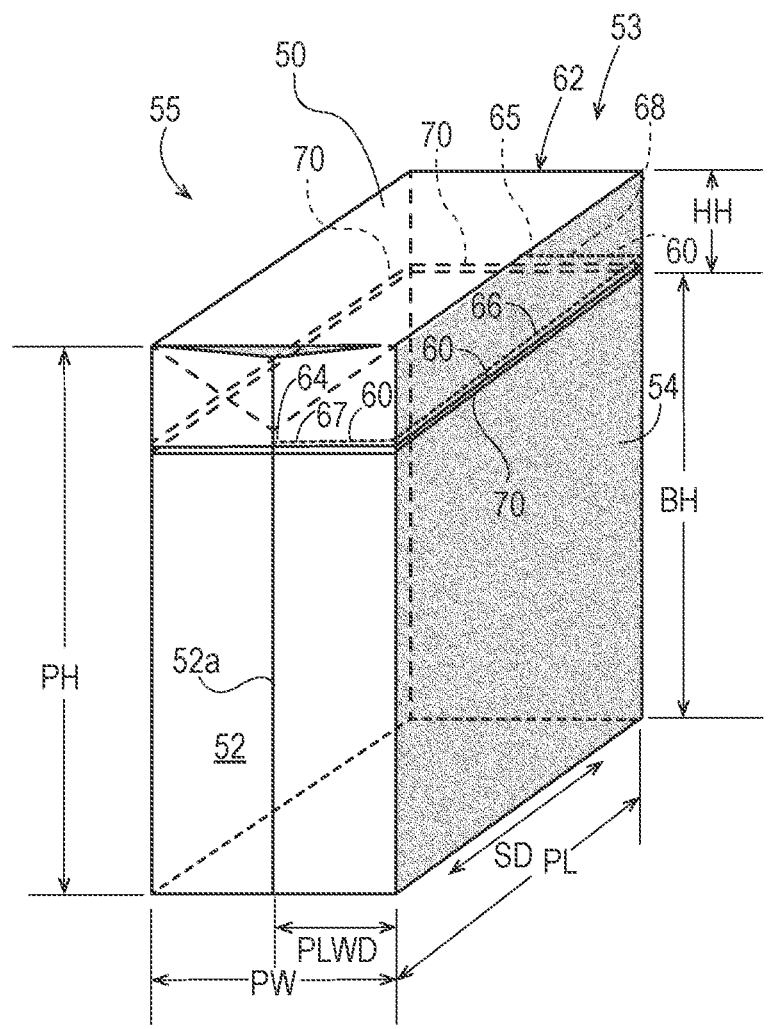
FIG. 7A is a perspective view of a film package that may be used to contain a stack of diapers such as the stack shown in FIG. 4, depicting a configuration of a line of weakness of perforations or scoring, in another example.

Referring to FIGS. 6A and 7A, a film package containing a stack of disposable absorbent articles such as disposable diapers, training pants or adult incontinence pants, may be imparted with features that facilitate opening without unwanted deformation or destruction of the package, so that the opened packaged may be used, following opening, as a container to store the supply of unused product.

In the examples depicted in FIGS. 6A and 7A, the package may be provided with a line of weakness 60 comprising, for example, perforations or scoring in the film. The line of weakness 60 may be continuous or discontinuous. For purposes herein, a "continuous" line of weakness of perforations or scoring is a singular line of weakness of individual, successive, mechanically-created partial or complete perforations, a singular line of weakness of individual, successive laser-scored partial or complete perforations, or a continuous, singular line of weakness of laser scoring, that is uninterrupted by an unperforated/unscored portion of the film of a length between successive perforations or scoring greater than 8 mm.

Figure 15:
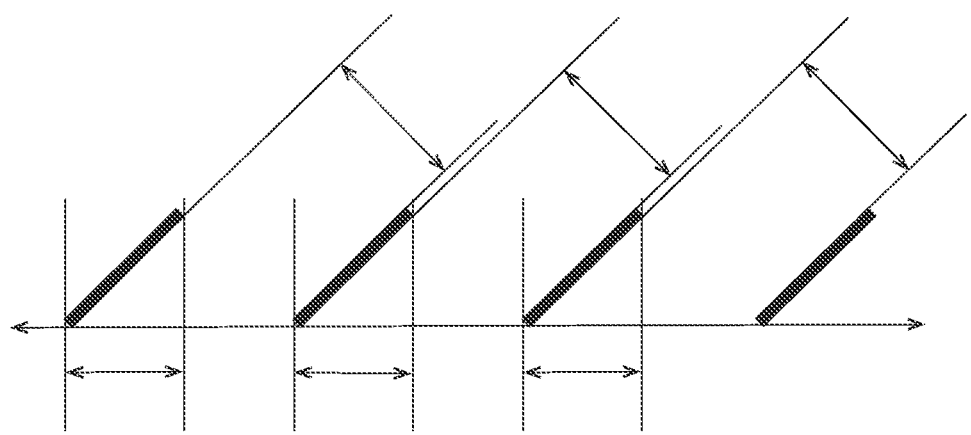
FIG. 15 is a schematic plan view depiction of an example of a configuration of perforations, illustrating measurements for determining cut-to-land ratio.

Individual perforations defining a line of weakness 60 may have any configuration suitable for propagating a tear in the package film along the line of weakness. Non-limiting examples are depicted in FIGS. 14A-14D. Where the line of weakness 60 comprises a plurality of individual mechanically-created perforations or individual laser-scored perforations, it may be desired that the line of weakness have a cut-to-land ratio of at least 0.67:1 and no greater than 3:1. For film packages of the type contemplated herein, it is believed that a cut-to-land ratio within this range strikes a suitable balance between providing for ease of package opening and minimized strain deformation of the film along the line of weakness during opening, and avoiding premature, unintended package bursting or opening, and retaining structural integrity of the package during shipping, handling and other events prior to retail purchase and intentional opening by the consumer. (For purposes herein, the "cut-to-land ratio" of a line of weakness of perforations is the ratio of the aggregate of the lengths of the perforations extending along the line of weakness direction, to the aggregate of the minimum distances of unperforated/unscored portions of the film between successive perforations. Referring to FIG. 15, for example, in which a portion of a line of weakness of successive diagonally-tilted rectangular perforations is depicted lying along line of weakness direction PD, the cut-to-land ratio is $(L1+L2+L3):(D1+D2+D3).L1$ In another example, the line of weakness may comprise a single, uninterrupted line of laser scoring that does not entirely penetrate the film (or all of layers of a multi-layer film) but is configured to promote neat tear propagation along the line of weakness, such as described in U.S. Application Pub. No. 2015/0266663, the disclosure of which is incorporated herein by reference.

For both ease of opening and simplification of manufacturing, it may be preferred that the line of weakness 60 does not traverse a gusset (such as gussets 52*b* and 53*b* ), because a gusset structure includes more than one layer of package film (e.g., three layers), making propagation of a neat tear along the line of weakness more difficult.

When the first side 41 of stack 40 is adjacent either the first package surface 50 or the second package surface 51, it may be desired that any portions of line of weakness 60 that traverse any of third, fourth, fifth or sixth package surfaces 52, 53, 54 and 55 be oriented at an angle that is 45 degrees or less, more preferably 30 degrees or less, even more preferably 15 degrees or less, and most preferably substantially parallel, with the approximate plane of the first side 41 of stack 40. This is because, as noted above, the film of package surfaces 52, 53, 54 and 55 will be in tension along directions substantially parallel with this plane, as the package contains the stack and maintains stack compression along the stacking direction SD. A line of weakness 60 on any of surfaces 52, 53, 54 and 55 that is substantially transverse to a direction of elevated film tension increases the risk of unintended, premature opening (rupture) of the package at a location along the line of weakness 60, prior to the time a consumer intends to open the package to access the contents. Accordingly, in the examples shown in FIGS. 6A and 7A, all portions of line of weakness 60, which are present on one of package surfaces 52, 53, 54 and/or 55, are oriented substantially parallel with the approximate plane of surface 50.

Figure 6B:
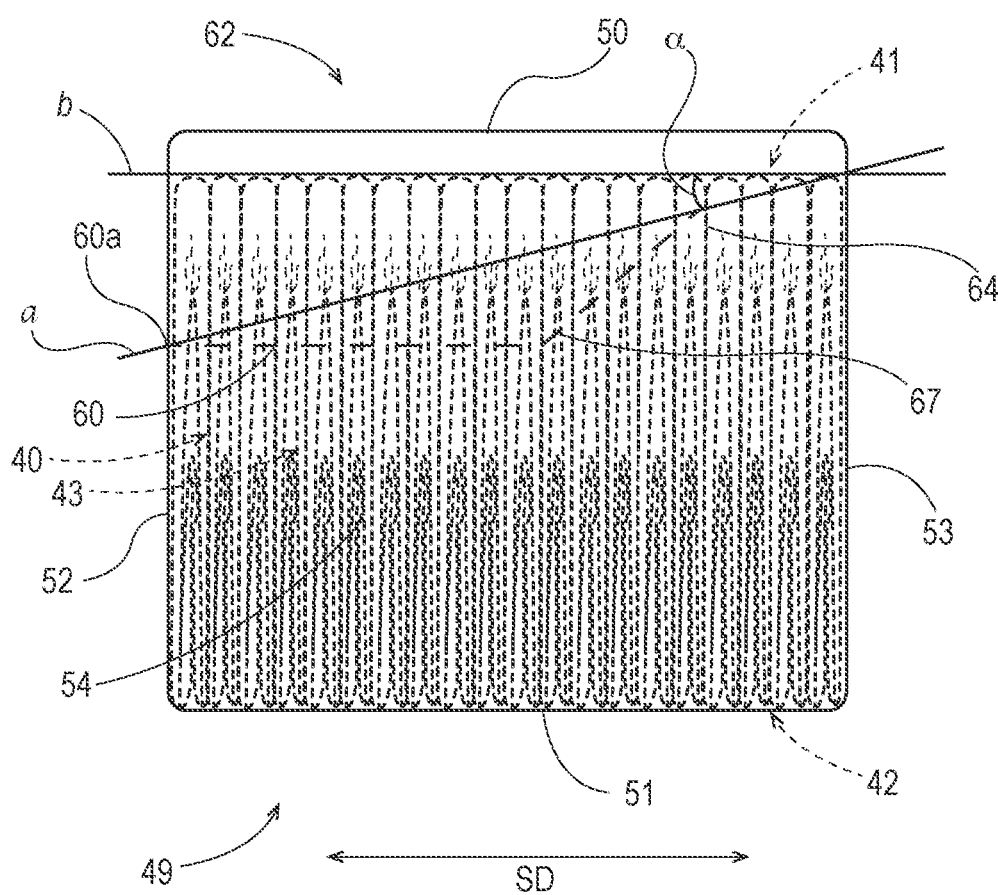
FIG. 6B is a side view of a film package that may be used to contain a stack of diapers such as the stack shown in FIG. 4, depicting a configuration of a line of weakness of perforations or scoring along the surface shown, in an alternative example.

In some examples, the manufacturer may choose to create a non-linear or non-uniformly linear line of weakness 60 in the package film. In one example depicted in FIG. 6B, line of weakness 60 has a portion 67 extending from corner point 60*a* where it traverses a package corner, to an endpoint 64. Portion 67 follows a non-linear line of weakness across fifth package surface 54. To observe the principles reflected in the preceding paragraph, a first straight line a is established, connecting corner point 60*a* and endpoint 64 of line of weakness 60. A second straight line b is established, parallel each of the planes along first 41 and third 43 sides of stack 40 within the package, and intersecting line a. Angle a at the intersection of lines a and b may then be measured, and is a reflection of the extent to which line of weakness 60 traverses the stacking direction SD. This method of measuring and determining the desired limitations on an angle of a line of weakness 60 across a package surface will apply to any line of weakness configuration, for purposes herein. For the reasons explained in the preceding paragraph, it may be desired that angle a be 45 degrees or less, more preferably 30 degrees or less, even more preferably 15 degrees or less, and most preferably approximately zero. Additionally, while an angle a greater than zero such as depicted in FIG. 6B may provide a hood structure 62 that is relatively easier to flip open following initial package opening (resulting from relatively less distance between endpoint 64 to an adjacent package surface, e.g., package surface 50), the free edge portions of hood structure 62 below line a will have less support within the hood structure following opening, making them less secure (i.e., floppy), which may in some circumstances be deemed counter to purposes of providing satisfactory reclosure.

To retain the utility of the package for serving as a container for unused product following opening, it may be desired that the line of weakness 60 of perforations or scoring leave an intact support band 70 about the perimeter of the package, extending across each of the third, fourth, fifth and sixth package surfaces 52, 53, 54 and 55. An intact support band 70 is an uncut, unperforated band of film material circumscribing the stack along a support plane approximately parallel to the plane of the first side 41 of the stack 40. For the package to be an effective container, it may be desired that support band 70 be located such that an unperforated portion of the package film surrounds and contains the stack 40 about at least half, or more, of its stack height. Accordingly, it may be desired that the support band 70 be located at a support band height BH of at least 50 percent, more preferably at least 55 percent, and even more preferably at least 60 percent of the stack height (SH) from the package surface 50 or 51 adjacent the second side 42 of the stack 40.

Line of weakness 60 demarcates a package base 61 and a package hood 62. After the package is initially opened the first absorbent article is retrieved, the package hood 62 can be converged with the package base 61 to cover over the remaining absorbent articles to help guard against entry of contaminants into the package. It has been discovered through experimentation and observation of consumer behavior that an opening hood structure 62 having three sides each formed of a portion of one of the third, fourth, fifth or sixth package surfaces 52, 53, 54, 55, and a top formed of a portion of one of the first or second package surfaces 50, 51, as suggested in FIGS. 6A and 7A, can provide an effective, easy to use cover over the supply of unused product. It has been discovered, surprisingly, that these configurations inherently promote consumer recognition and use of them as reclosing devices. In the example depicted in FIG. 6A, a hood structure 62 has three sides formed of portions of package surfaces 52, 54 and 55, and the top is formed by a portion of first package surface 50. In the example depicted in FIG. 7A, a hood structure 62 is formed of portions of package surfaces 52, 53 and 54, and the top is formed by a portion of first package surface 50. The hood structure is formed when the consumer tears the package film completely along line of weakness 60 of perforations or scoring. After opening, the hood structure 62 may be reclosed by returning it to a position similar to the one it occupied with respect to the remainder of the package, prior to opening.

Through experimentation and observation of consumer behavior, it believed that the hood structure 62 preferably provides quick access and retrieval, using one's fingers, following package opening, for a majority of the individual articles in the stack 40, without requiring a reach far down inside the package. From observation it is believed that the proximity of the fold noses to the opening is preferred by consumers because it reduces effort by facilitating the quick tactile identification and grasping of an individual product for withdrawal from the stack and from the package. Thus, in the example depicted in FIG. 6A (herein designated a "long-short-long" or "LSL" line of weakness 60), the portions 67, 68 of line of weakness 60 defining the hood may have a stack direction line of weakness length PLSD of at least 60 percent, more preferably at least 65 percent, even more preferably at least 70 percent, of the package length (PL). At the same time, it may be desired that the hood structure not lift entirely away from the top of the stack, because this may reduce consumer recognition and use of the hood structure as a reclosing/covering device. Accordingly, in the example depicted in FIG. 6A, the portions 67, 68 of line of weakness 60 defining the hood may have a stack direction line of weakness length PLSD limited at 95 percent, more preferably 90 percent, and even more preferably 85 percent, of the package length (PL).

Through the above-referenced experimentation and observations, it is believed that consumers prefer the hood structure to have at least a minimum amount of material to grasp and pull back over the unused supply of articles in the package in the manner of a hood. Thus, in order for the LSL hood structure 62 such as depicted in FIG. 6A to have an appearance and function as such, it may be desired that the structure have a hood height HH of at least 40 mm, more preferably at least 45 mm and even more preferably at least 50 mm.

FIG. 7A depicts an example of a line of weakness configuration (herein designated a "short-long-short" or "SLS" line of weakness 60). The entire length of the stack 40 will be exposed for access upon opening along line of perforations or scoring 60, but only a portion of the width of the stack will be exposed. For reasons similar to those expressed above, it may be desired that the hood structure 62 not lift entirely away from the top of the stack. Accordingly, in the SLS example depicted in FIG. 7A, the portions of line of weakness 60 defining the hood structure may have a width direction line of weakness length PLWD of at least 25 percent, more preferably at least 35 percent, even more preferably at least 45 percent of the stack width SW, but not more than 75 percent, more preferably not more than 60 percent, more preferably not more than 50 percent, of the stack width SW, and even more preferably not extending past a side seam 52a, 53a.

For reasons similar to those expressed above, in order for the SLS hood structure 62 such as depicted in FIG. 7A to have an appearance and function as such, it may be desired that the structure have a hood height HH of at least 50 mm, more preferably at least 60 mm, and even more preferably at least 70 mm.

For purposes herein, the hood height HH is measured with the stack 40 within the package urged all the way within the package (without adding any substantial compression of the stack height), against the first or second package surface 50 or 51 opposite the hood structure. With the stack urged to this position, and the package standing with its height vertical, the hood height HH is the largest measurable distance between the line of weakness 60 of perforations or scoring where it traverses a package corner, and the nearest of the first or second sides 41, 42 of the stack (which during measurement with the package standing as described, will be proximate the apparent "top" relative the top-opening hood structure). See, e.g., FIG. 7B.

In another example, the package may comprise a combination of a LSL line of weakness 60 and a SLS line of weakness 60. Thus, in reference to both FIGS. 6A and 7A, the perforation line of weakness 60 can extend from end point 65 on package surface 55, as shown in FIG. 6A, extend completely across package surfaces 52 and 54, and extend to end point 65 on package surface 53, as shown in FIG. 7A. Such a perforation line of weakness combination can lead to two possible scenarios. The first scenario creates a choice for the consumer to create and use a hood structure 62 via LSL line of weakness 60 or a hood structure 62 via SLS line of weakness 60. The second scenario creates a greater opening and more flexible hood structure 62 when the consumer tears the package along the combined LSL line of weakness 60 and SLS line of weakness 60. Additional line of weaknesses are contemplated herein to effect a combination LSL line of weakness and SLS line of weakness. The perforation line of weakness 60 in the first scenario may optionally comprise features tearing stress dispersion features, as described below with reference to FIG. 8, or other features that limit tearing to the consumer choice of either LSL line of weakness 60 or SLS line of weakness 60 upon opening the package.

Figure 7B:
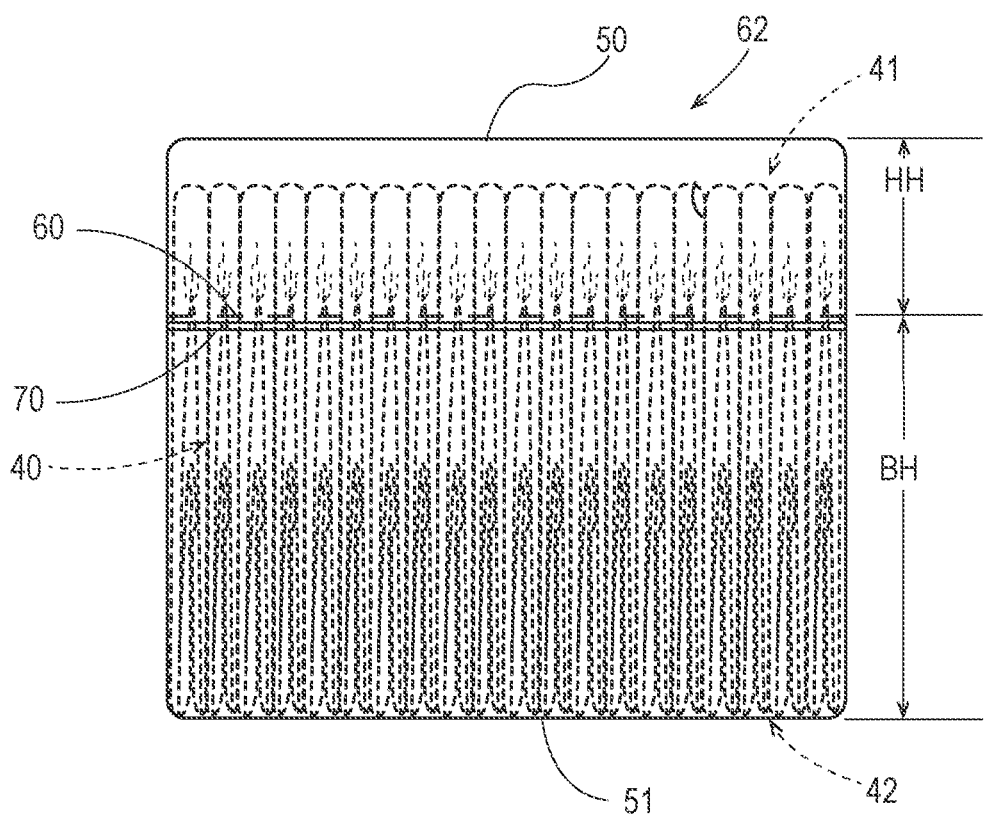
FIG. 7B is a side view of a film package that may be used to contain a stack of diapers such as the stack shown in FIG. 4, depicting a configuration of a line of weakness of perforations or scoring along the surface shown, and illustrating measurement of hood height.

In some examples it may be preferred that the package include some head space therewithin, and within the hood structure. This is illustrated in FIG. 7B, depicting head space within the package above side 41 of stack 40. This results in some slack film material in the hood structure prior to package opening. This extra material provided along the direction of the package height gives the consumer extra material to conveniently grasp when reclosing the package with the hood structure. Additionally, the extra film material along the direction of the package height enables the consumer to pull the hood structure down over the stack and down over and beyond the support band 70 and/or down below the line of weakness perforations or scoring on the lower portion of the package, easily and conveniently overlapping some of the film material of the hood structure over the film material below the line of weakness 60, providing for more complete reclosure and more complete coverage of the unused supply of product within the package.

Figure 8:
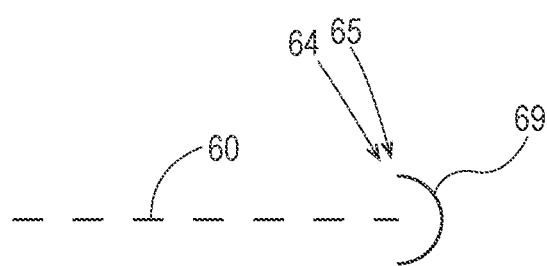
FIG. 8 is a depiction of an endpoint of a line of weakness of perforations or scoring, including a tearing stress dispersion feature.

Referring to FIG. 8, in order to reduce chances that a consumer opening the package will tear the package film past endpoints 64, 65 of the line of weakness 60 of perforations or scoring, and deform the package film and/or reduce the utility of the hood structure 62, it may be desired to include a tactilely perceivable tearing stress dispersion feature 69 proximate one or both endpoints 64, 65. In the example depicted in FIG. 8, tearing stress dispersion feature 69 is a semi-circular perforation or cut running transverse to the direction of the line of weakness 60, which serves to disperse tearing stresses concentrated at the endpoint, and obstruct tear propagation in a way that may be perceived tactilely by the consumer they are opening the package. It will be appreciated that tearing stress dispersion feature 69 may have other forms including other shapes of cuts or perforations through the film that extend transversely to the direction of the line of weakness 60, added reinforcing strips, tapes, etc.

Stress dispersion features can also be placed at varying points along a line of weakness of perforations or scoring besides the end points. This approach can permit relatively small openings and hood structures. For example, some consumers (e.g., hygiene-sensitive consumers who seek to open the packaging minimally for protection, or those who invest in minimal effort to open and close the package) utilize a corner lift that is enabled by a LSL line of weakness or combination LSL and SLS line of weakness. While these lines of weakness can enable a corner lift, employment of stress dispersion features can maintain the desired size of the opening and corresponding hood structure.

It may be desired to provide one or more indicia on the package that visibly, tactilely and/or verbally identify the location of the line of weakness 60 of perforations or scoring. The one or more indicia may include, but are not limited to, an imprinted line of weakness marking or tracing line of weakness 60, of a color that visibly contrasts with surrounding package printing; tactilely perceivable indicia; verbal indicia; other graphic indicia or any combination thereof. In one example, the indicia may include embossing or other surface texturing of the film, configured to provide raised, tactilely perceivable features that suggest the presence of the line of weakness 60.

Graspable Tab and Reinforcement Members

Figure 9:
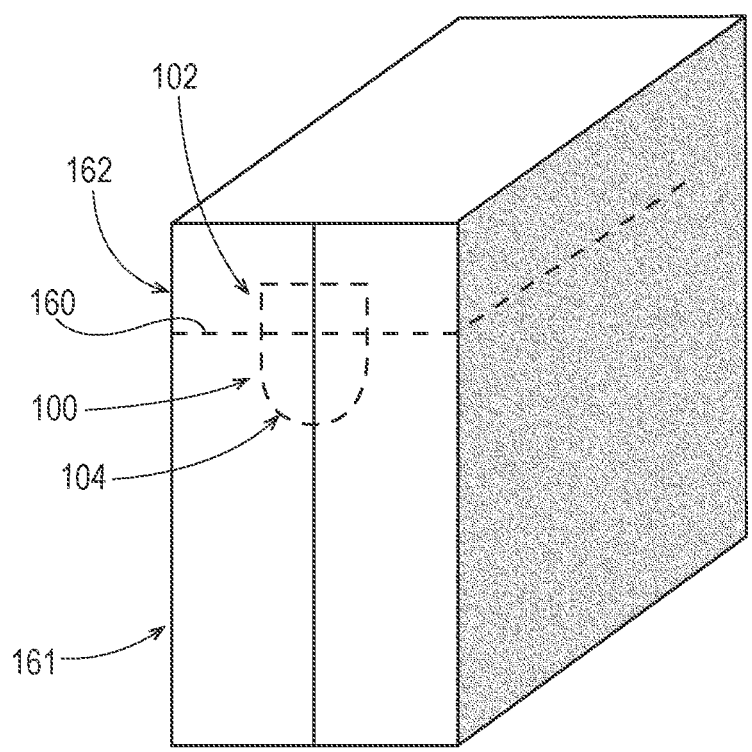
FIG. 9 is a perspective view of a film package that may be used to contain a stack of diapers such as the stack shown in FIG. 4. A hidden tab is included and attached on a hood portion of the package. A graspable portion of the tab is revealed when the package is opened the first time and can be used to reclose the package after a diaper is retrieved form the package.
Figure 10:
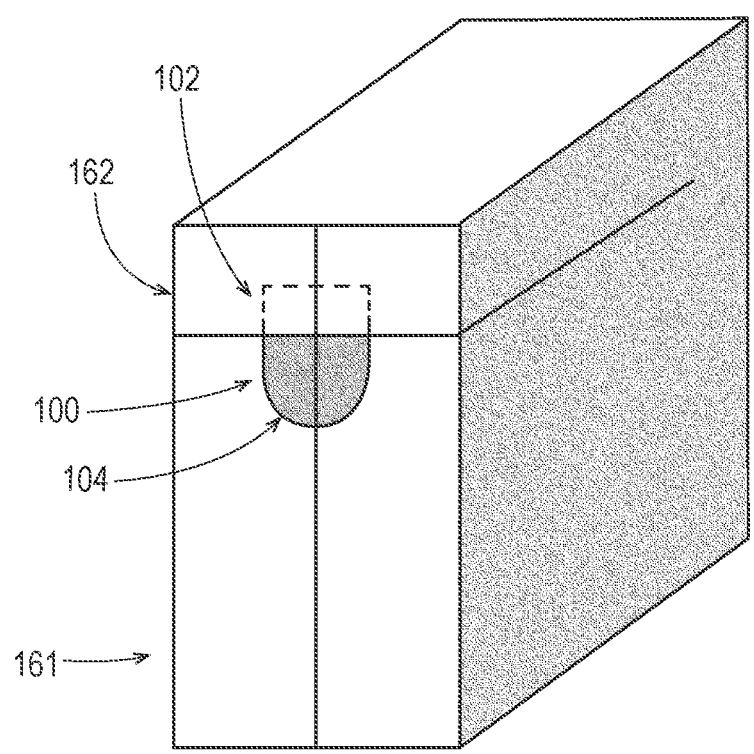
FIG. 10 is a perspective view of the film package of FIG. 9 after it has been opened and the hood closed back via the tab.

Additional material and/or features can optionally be employed on at least one of an interior film surface and an exterior film surface to provide further functionality to the packages. With reference to FIGS. 9 and 10, a tab 100 can be employed on the package to help consumers reposition the hood 162 over the unused absorbent articles after one of the articles is removed from the package. Tab 100 includes a fixed portion 102 that is affixed to the package, and a graspable portion 104 that extends from an edge of hood 162. Fixed portion 102 can be affixed to the package by any number of techniques, including, for example, through adhesive, ultrasonics, heat, pressure, and combinations thereof. In one example and as shown in FIG. 9 both fixed portion 102 and graspable portion 104 are disposed within an interior of the package prior to an initial opening of the package. A consumer opens the package through manipulation of at least part of the line of weakness 160, lifts hood 162, and then retrieves one of the absorbent articles. Graspable portion 104 is discovered by the consumer as the hood 162 is lifted. The consumer can then reclose the package by engaging graspable portion 104 to help reposition hood 162 to be adjacent the package base 161. As hood 162 is pulled back over the exposed portions of remaining absorbent articles and back towards base 161, graspable portion 104 is positioned on the exterior of the package, as shown in FIG. 10. In an alternative example, graspable portion 104 can be positioned on the exterior of the package both prior to and after the initial opening of the package. Graspable portion 104 extends beyond an edge of hood 162 a suitable distance; for example, 2-15 centimeters, and preferably no more than 4, 5, or 6 centimeters. In one form, the bending stiffness or rigidity of the graspable portion 104 is greater than that of the flexible polymeric film from which the main package is constructed. The tab and/or portions thereof can be made from a variety of materials, including, for example, woven fibrous materials, nonwoven fibrous materials, polymeric films, nonwoven/film laminates, paperstock, scrims, and the like.

Tab 100 may be positioned on a package surface/panel that comprises a seam and/or gusset. While fixed portion 102 may be directly attached to the seam and/or gusset, it preferably avoids the same. A single tab can be positioned wherein the fixed portion of the same is located on one side of a seam and/or gusset, or it can employ of fixed portion that includes two spaced apart sections that can affixed to a package surface/panel on either side of seam and/or gusset. Alternatively, multiple tabs can be employed and positioned on different locations on a single surface/panel (e.g., on either side of a seam and/or gusset), or on multiple package surfaces/panels. Use of multiple tabs can also help manage stress and strain on any given portion of the package hood to permit different material and design choices.

Hood 162 will generally remain in place once repositioned unless forces act upon the hood to displace it. For consumers wanting a more secure placement of hood 162, the graspable portion may comprise a fastening feature. For example, graspable portion 104 may comprise pressure sensitive adhesive that can facilitate the graspable portion 104 positively engaging the packaging film in package base 161. In the scenario where graspable portion 104 is initially disposed in the interior of the package, a release liner may overlay the pressure sensitive adhesive such that the adhesive does not stick to an interior surface of the package or to one of the absorbent articles. Release liners can comprise silicone coated paper for example. After opening the package, the consumer would simply peel the release liner off to begin using the tab and its fastening feature to close the hood and to secure it in place. It can be advantageous for the graspable portion to be devoid of a fastening feature. Absence of a fastening feature can simplify the operation of the tab and/or eliminate additional material for disposal.

Figure 11:
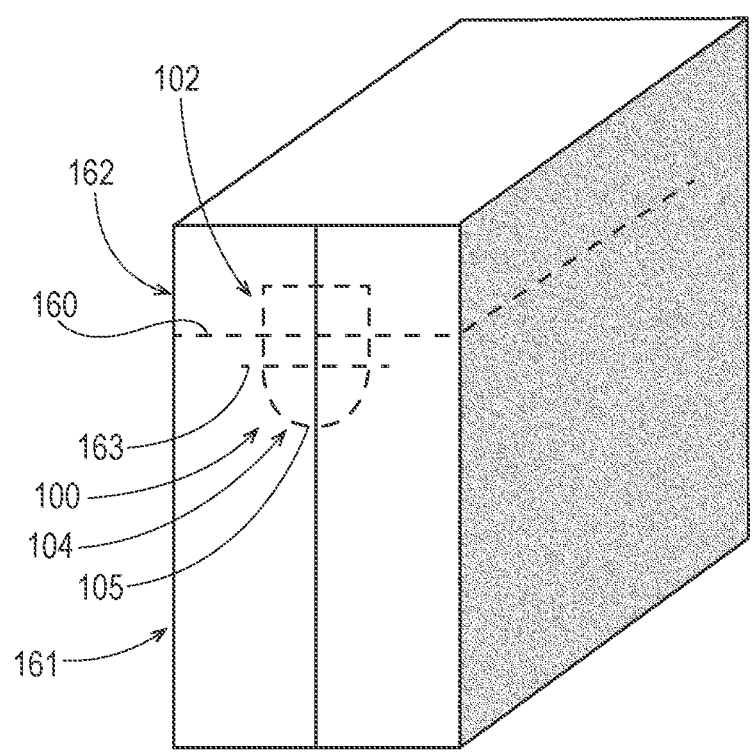
FIG. 11 is a perspective view of a film package that may be used to contain a stack of diapers such as the stack shown in FIG. 4. A hidden tab is included and attached on a hood portion of the package. A graspable portion of the tab is revealed when the package is opened the first time and can be used to reclose the package after a diaper is retrieved form the package.
Figure 12:
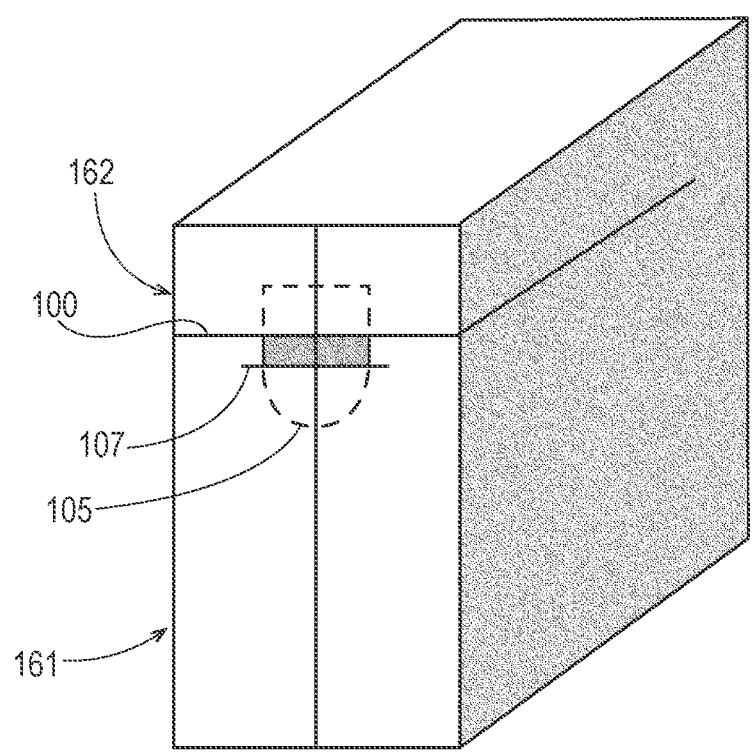
FIG. 12 is a perspective view of the film package of FIG. 11 after it has been opened and the hood closed back via the tab. A distal end of the tab is tucked into a slot to securely retain the hood in a closed position.

Secure positioning of the package hood can be accomplished through techniques other than employing a fastening feature to the tab's graspable portion. For example and with reference to FIGS. 11 and 12, one or more slits 107 (shown in FIG. 12) within the package base 161 can accept a distal end 105 of graspable portion 104. If one slit is employed, then distal end 105 can be tucked into the slit and thereby reside within the package interior. If multiple slits are employed, the slits can act like a buckle for receiving distal end 105. Such slits can exist in the package as purchased, or they can be activated by consumers once the package is purchased via additional line(s) of weakness such as perforation 163 (shown in FIG. 11).

Additional material and features can also be employed for improving the structural integrity of the package. A reinforcement member can disposed on an exterior surface of the package and/or on an interior surface of the package. In one example, the reinforcement member is disposed proximate the line of weakness. The reinforcement member can be made from a variety of materials, including one or more elastomeric bands or strands, a strip or layer of foam, a fibrous web (nonwoven or woven), a scrim, a magnetic substrate, a polymeric film, a bead, line or patterned deposit of cured polymer (with or without magnetic properties) or hot-melt adhesive formulation (with or without a tackifier). Fibrous webs or scrims can comprise natural fibers (e.g., cotton or wood pulp), synthetic fibers, or a combination thereof. The fibrous web can be made through a wet laid process or a dry laid process. The reinforcement member can affixed to the package by any number of techniques, including, for example, through adhesive, ultrasonics, heat, pressure, and combinations thereof.

The reinforcement member can be included in the hood, the base, or both. With reference to FIG. 13, a package surface 153 comprises a first reinforcement member 112 on the package base 161 and a second reinforcement member 114 on the package hood 162. Properties and characteristics of first reinforcement member 112 and second reinforcement member 114 can be the same, or can be different. Exemplary differences are described in more detail below.

First reinforcement member 112 and second reinforcement member 114 can comprise different materials. For example, reinforcement member 112 may be made from a material having a relatively higher coefficient of friction to help hold the absorbent articles in place within the package base 161, while reinforcement member 114 may be made from a material having a relatively lower coefficient of friction to facilitate the hood 162 sliding over the absorbent articles when hood 162 is repeatedly opened to retrieve an absorbent article and then subsequently closed.

Dimensions and location of two or more reinforcement members can also vary. Reinforcement members 112 and 114 comprise a length RML1 and RML2, respectively, and a height RMH1 and RMH2, respectively. In FIG. 13, lengths RML1 and RML2 extend in a direction substantially parallel to line of weakness 160, and heights RMH1 and RMH2 extend in a direction substantially orthogonal to line of weakness 160. Length RML1 may be the same or different than length RML2. And lengths RML1 and RML2 may extend to similar lengths or different lengths than that of the line of weakness 160. Since the line of weakness preferably extends around less than 100%, 90%, or 80% of the package perimeter to maintain the hood feature, an employed reinforcement member may extend to a length that is greater than the line of weakness including extending around the entire or substantially the entire perimeter of the package hood or base. Height RMH1 may be the same or different than height RMH2. When they are different, a ratio of 1.5:1 or greater can be beneficial. Similarly, the two or more reinforcement members can have a different thickness. In one example, first reinforcement member 112 may be thicker than second reinforcement member 114 to help keep the stack of absorbent articles more taut and/or help create a resting stop for hood 162. Exemplary heights RHM1 and RHM2 can range from 1, 2, or 5 mm to 10, 20, 30, or 50 mm. Other heights are also contemplated.

Figure 13A:
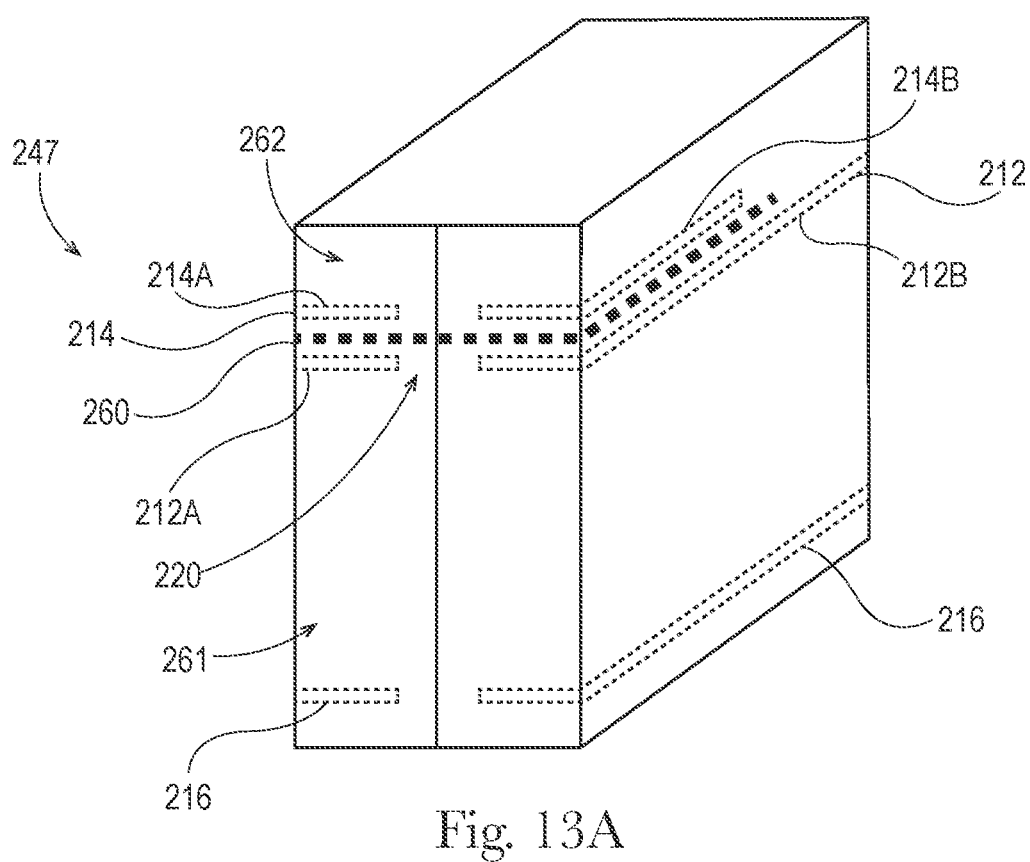
FIG. 13A is a perspective view of a package showing a line of weakness, and a first and second reinforcement member.

FIG. 13A illustrates a package 247 comprising a seam 250, a line of weakness 260, a first reinforcement member 212 situated below line of weakness 260 on base 261, and a second reinforcement member 214 situated above line of weakness 260 on hood 262. First reinforcement member 212 comprises a first portion 212A and a second portion 212B. Similarly, second reinforcement member 214 comprises a first portion 214A and a second portion 214B. This arrangement creates a window 220 proximate package seam 250 wherein a reinforcement member does not exist. First reinforcement member 212 is shown comprising a length that is longer than that of line of weakness 260, while second reinforcement member 214 is shown comprising a length that is shorter than that of line of weakness 260—this can create a flexible hinge effect for opening and closing hood 262. Note that in an alternative arrangement, first reinforcement member 212 can comprises a length that is longer than that of line of weakness 260, but shorter than a length of second reinforcement member 214. One can also observe in FIG. 13A that the reinforcement members are proximate to but spaced apart from line of weakness 260.

FIG. 13A also shows an optional third reinforcement member 216 situated on a lower portion of base 261 (e.g., about ½ or ¾ of way down the base as measured from the line of weakness). Third reinforcement member 216 can improve the standing stability of package 247. In some forms, the package may comprise one or more reinforcement members positioned and configured for providing structural stability to the package while not including a reinforcement member proximate the line of weakness as shown herein.

In another example, a single reinforcement member is sized and positioned to span the line of weakness, wherein the reinforcement member is partially attached to the package hood so as to define a free portion of the reinforcement member. The free portion of the reinforcement member extends beyond a lower edge of the package hood after the package is opened to cover an upper edge of the package base. In yet another example, a single reinforcement member that spans the line of weakness may be separated into two reinforcement members, one on either side of an opening once the package is opened; that is, the both the package material and the reinforcement member are frangibly separated upon opening the package.

The graspable tab and/or reinforcement member can optionally comprise other features and benefits beyond their primary function and benefit. For example, the tab and/or reinforcement member can comprise an additive, such as, a fragrance or odor management material. The odor management material is intended to manage odors inherently flowing from raw materials used in the manufacture of the contained absorbent articles, the raw materials used in the manufacture of the package, or both. Useful odor management materials include activated carbon, zeolites, and cyclodextrins. The tab and/or reinforcement member can also employ marketing materials, such as, for example, product information regarding the contained absorbent articles or coupons for the future purchase of the absorbent articles or a different product offered by the manufacturer.

Handle

It may be desired that the package include a carrying handle. In one example, a carrying handle may be formed of a strip of polymer film. The strip may be bonded by any suitable mechanism to portions of the package or package film. In another example, a carrying handle may be formed of an extension of a fin extending from the package from an end seam. The end seam fin may have a handle cutout made therethrough, providing a carrying handle.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

I claim:

1. A package formed of flexible polymeric film, the package comprising:
   a. a plurality of absorbent articles;
   b. the flexible polymeric film enclosing the plurality of absorbent articles to define the package;
   c. a line of weakness imparted into the flexible polymeric film to facilitate opening the package and to demarcate a package base and a package hood; and
   d. a reinforcement member comprising a strip of material disposed on at least one of the package base or the package hood, wherein the package has a package height, and wherein the reinforcement member is spaced apart from the line of weakness along the package height.

2. The package of claim 1, wherein the reinforcement member is disposed on an interior surface of the flexible polymeric film.

3. The package of claim 1, wherein the reinforcement member comprises a fibrous web.

4. The package of claim 1, wherein the reinforcement member comprises recycled material.

5. The package of claim 1, wherein the reinforcement member comprises a material that imparts reinforcement to the flexible polymeric film.

6. The package of claim 1, wherein the reinforcement member comprises material that is different from the flexible polymeric film.

7. The package of claim 1, wherein the reinforcement member does not include a line of weakness.

8. The package of claim 1, wherein the strip of material has a length longer than a length of the line of weakness.

9. The package of claim 1, wherein the strip of material has a length shorter than a length of the line of weakness.

10. The package of claim 1, wherein the reinforcement member is affixed to the flexible polymeric film with adhesive.

11. The package of claim 1, wherein the line of weakness extends around less than 100% of a perimeter of the package.

12. The package of claim 1, wherein the line of weakness extends around less than 80% of a perimeter of the package.

13. The package of claim 1, wherein the reinforcement member comprises a higher bending stiffness than the flexible polymeric film.

14. The package of claim 1, wherein the reinforcement member comprises a first reinforcement member disposed on the package base and a second reinforcement member disposed on the package hood.

15. The package of claim 14, wherein the first reinforcement member is different from the second reinforcement member.

16. A package formed of flexible polymeric film, the package comprising:
   a. a plurality of absorbent articles;
   b. the flexible polymeric film enclosing the plurality of absorbent articles to define the package;
   c. a line of weakness imparted into the flexible polymeric film to facilitate opening the package and to demarcate a package base and a package hood;
   d. a first reinforcement member comprising a strip of material disposed on an interior surface of the package base and spaced apart from and proximate the line of weakness;
   e. a second reinforcement member comprising a strip of material disposed on an interior surface of the package hood and spaced apart from and proximate the line of weakness; and
   f. wherein the first and second reinforcement members do not include a line of weakness.

17. The package of claim 16, wherein the first reinforcement member is different from the second reinforcement member.

18. The package of claim 16, wherein a length of at least one of the first reinforcement member or the second reinforcement member is different than a length of the line of weakness.

19. The package of claim 16, wherein the first reinforcement member has a height and/or length different than a height and/or length of the second reinforcement member.

20. A package formed of flexible polymeric film, the package comprising:
   a. a plurality of absorbent articles;
   b. the flexible polymeric film enclosing the plurality of absorbent articles to define the package;
   c. a line of weakness imparted into the flexible polymeric film to facilitate opening the package and to demarcate a package base and a package hood; and
   d. a reinforcement member comprising a strip of material disposed on an interior or exterior surface of the package and spaced apart from and proximate the line of weakness;

e. wherein the package comprises a seam;
f. wherein the reinforcement member does not overlap the seam; and wherein the reinforcement member does not include a line of weakness.

* * * * *